United States Patent [19]

Sugama et al.

[11] Patent Number: 5,492,611

[45] Date of Patent: Feb. 20, 1996

[54] MINIATURIZED OXYGEN ELECTRODE

[75] Inventors: Akio Sugama; Hiroaki Suzuki; Naomi Kojima, all of Kawasaki, Japan

[73] Assignee: Fujitsu Limited, Kawasaki, Japan

[21] Appl. No.: 307,013

[22] Filed: Sep. 16, 1994

Related U.S. Application Data

[60] Continuation-in-part of Ser. No. 145,245, Nov. 3, 1993, which is a division of Ser. No. 850,834, Mar. 13, 1992, Pat. No. 5,281,323.

[30] Foreign Application Priority Data

Mar. 20, 1991 [JP] Japan .................................. 3-057220
May 28, 1991 [JP] Japan .................................. 3-123787

[51] Int. Cl.$^6$ ................................................ G01N 27/26
[52] U.S. Cl. ........................ 204/415; 204/403; 204/414; 204/418; 204/419
[58] Field of Search .................................. 204/403, 415, 204/153.17, 418, 419, 433, 435, 414

[56] References Cited

U.S. PATENT DOCUMENTS

| | | | |
|---|---|---|---|
| 4,001,042 | 1/1977 | Trocciola et al. | 427/115 |
| 4,496,451 | 1/1985 | Isshii et al. | 204/252 |
| 4,699,804 | 10/1987 | Miyata et al. | 427/255.6 |
| 4,874,500 | 10/1989 | Madou et al. | 204/412 |
| 4,909,912 | 3/1990 | Oda et al. | 204/98 |
| 4,975,175 | 12/1990 | Karube et al. | 204/403 |
| 5,133,856 | 7/1992 | Yamaguchi et al. | 204/415 |

FOREIGN PATENT DOCUMENTS

| | | |
|---|---|---|
| 0030503 | 6/1981 | European Pat. Off. . |
| 100667 | 2/1984 | European Pat. Off. . |
| 284518 | 9/1988 | European Pat. Off. . |
| 2-236154 | 9/1990 | Japan . |
| 2-240556 | 9/1990 | Japan . |

OTHER PUBLICATIONS

*Patent Abstracts of Japan*, vol. 11, No. 223 (P-597), Jul. 21, 1987 (JP 62-039755, Feb. 20, 1987.).

Inspec Database Abstract No. A86097437, Institute of Electrical Engineers, London, GB; S. J. Pace et al.: "A thick-film multi-layered oxygen sensor" & Transducers'85–1985 International Conference On Solid State Sensors & Actuators Digest Of Technical Papers (Cat. No. 85CH2127–9) 1985, IEEE, New York, NY pp. 406–409. no month available.

World Patents Index Latest Derwent Publications Ltd., London, GB; Database WPIL Accession No. 90-330569, week 9044 (JP-A-2-236154, Aug. 19, 1990).

*Patent Abstracts of Japan*, vol. 14, No. 554 (P-1140), Mar. 9, 1989 (JP-A-2-236154, Aug. 19, 1990).

*Primary Examiner*—Bruce F. Bell
*Attorney, Agent, or Firm*—Staas & Halsey

[57] ABSTRACT

A miniaturized oxygen electrode comprising: an electrically insulating substrate; an electrolyte-containing material disposed on the substrate to form an electrolyte solution when water is introduced thereto; a set of component electrodes disposed on the substrate and connected with each other via the electrolyte-containing material; a gas-permeable membrane covering the electrolyte-containing material; the set of component electrodes including a cathode on which a reduction reaction of oxygen occurs and an anode as a counterpart of the cathode; the electrolyte-containing material being composed of a first layer and a second layer which are mutually connected, the first layer containing no electrolytes and being connected to the cathode and the second layer containing an electrolyte and being not connected to the cathode, the mutual connection of the first layer and the second layer being effected so that, during the water introduction and a subsequent holding, the electrolyte of the second layer diffuses to the first layer to form a single electrolyte solution layer.

18 Claims, 38 Drawing Sheets

(PART OF SECTION TAKEN ALONG LINE I–I OF Fig.2(a))

I-I SECTION

PLAN VIEW

I-I SECTION

PLAN VIEW

I-I SECTION

PLAN VIEW

I-I SECTION

PLAN VIEW

I-I SECTION

PLAN VIEW

PLAN VIEW (ENTIRE WAFER)

I-I SECTION

PLAN VIEW (ENTIRE WAFER)

I-I SECTION

PLAN VIEW (ENTIRE WAFER)

I-I SECTION

PLAN VIEW (ENTIRE WAFER)

Fig.8(a)
Fig.8(b)
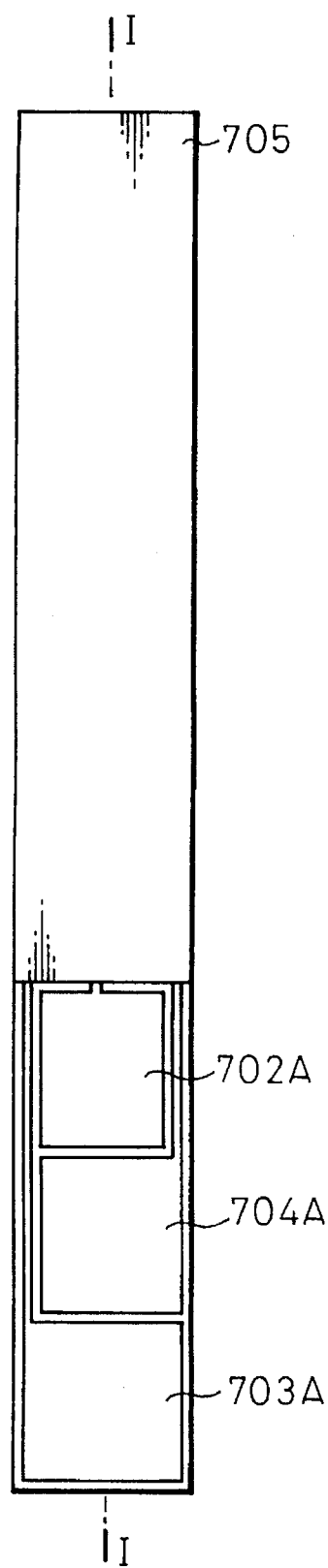
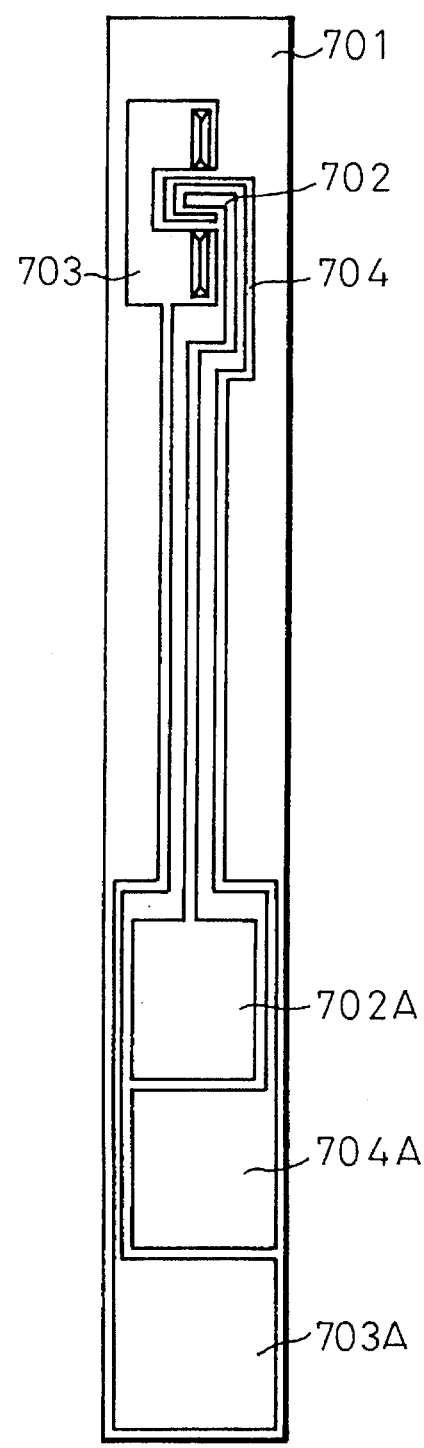

(PART OF SECTION TAKEN ALONG LINE I-I OF Fig.8(a))

I-I SECTION

PLAN VIEW

I-I SECTION

PLAN VIEW

I-I SECTION

PLAN VIEW

I-I SECTION

PLAN VIEW

I-I SECTION

PLAN VIEW

MINIATURIZED OXYGEN ELECTRODE

CROSS-REFERENCES TO RELATED APPLICATIONS

This application is a continuation-in-part application of U.S. Ser. No. 08/145,245 filed on Nov. 3, 1993, which is a divisional application of U.S. Ser. No. 07/850,834 filed on Mar. 13, 1992, now U.S. Pat. No. 5,281,323.

BACKGROUND OF THE INVENTION

1. Field of the Invention

The present invention relates to a diaphragm-type miniaturized oxygen electrode, more particularly, to a miniaturized oxygen electrode useful for many applications including a measurement of the dissolved oxygen concentration of a solution, to an electrolyte composition suitable for forming the sensing site of the miniaturized oxygen electrode, and to a process of mass-producing miniaturized oxygen electrodes having a uniform quality.

An oxygen electrode is very useful for measuring the dissolved oxygen concentration in many fields. For example, oxygen electrodes are used in the field of water control, the BOD (Biochemical Oxygen Demand) in water is measured, and in the fermentation and brewing field, the dissolved oxygen concentration of a fermentation tank or fermenter is measured, to ensure an efficient fermentation of alcohol, etc.

An oxygen electrode can be combined with an enzyme to form a biosensor or an enzyme electrode to be used for measuring the concentration of sugar, vitamins, etc. For example, an oxygen electrode can be combined with glucose oxidase to measure the concentration of glucose or grape sugar. This utilizes a phenomenon in which glucose is oxidized by the dissolved oxygen with the aid of a catalytic action of glucose oxidase to form gluconolactone, with a resulting reduction of the dissolved oxygen amount diffusing into an oxygen electrode.

In addition to the measurement of the dissolved oxygen concentration of a solution, an oxygen electrode can be advantageously used for controlling the oxygen concentration of a gas phase. For example, a reduction of the ambient oxygen concentration to below 18% causes a dangerous oxygen deficiency, and in medical-care equipment, such as oxygen inhalation and gas anesthetization, the oxygen concentration of a gas used must be strictly controlled.

The oxygen electrode is thus very advantageously used in many fields, including environmental instrumentation, the fermentation industry, clinical care, and industrial hygiene.

2. Description of the Related Art

The conventional oxygen electrode typically has a structure as shown in FIG. 1, wherein a vessel or container 118 made of glass, plastics, stainless steel, or the like has an open end (lower end) covered and sealed with an oxygen gas-permeable membrane 107 made of silicone resin, fluororesin or the like, and an aqueous solution 119 of potassium chloride (KCl), sodium hydroxide (NaOH), etc., is filled in the vessel 118, in which an anode 104 made of silver (Ag), lead (Pb), etc., and a cathode 105 made of platinum (Pt), gold (Au), etc., are arranged.

The conventional oxygen electrode has a complicated structure, and therefore, it is difficult not only to miniaturize but also to mass-produce same.

The present inventors and others have proposed a new type of miniaturized oxygen electrode that can be produced by utilizing a semiconductor production process including a photolithography and an anisotropic etching, as disclosed in Japanese Unexamined Patent Publication (Kokai) No. 63-238,548 and U.S. Pat. No. 4,975,175.

The proposed oxygen electrode has a structure as shown in FIGS. 2 and 3, in which FIG. 2(b) shows an unfinished structure in which an oxygen gas-permeable membrane is not yet formed. This structure is produced by the following sequence. Two grooves 202 to be filled with an electrolyte-containing material are formed on a silicon wafer 201 by an anisotropic etching and the wafer surface is then covered by an $SiO_2$ insulating layer 203 to form an electrically insulating substrate. Then, two component electrodes, i.e., an anode 204 and a cathode 205, are formed on the insulating layer 203. The anode 204 has one end 204A for external electrical connection and the other end of two branches extending into the grooves 202. The cathode 205 has one end 205A for external electrical connection and the other end extending to the top surface of a plateau retained between the grooves 202. An electrolyte-containing material 206 is filled in the grooves 202, and the filled electrolyte-containing material 206 is in contact with the anode 204 within the grooves 202 and with the cathode 205 on the plateau. The upper surface of the filled electrolyte-containing material 206 is then covered with an oxygen gas-permeable membrane 207.

Nevertheless, the step of filling the grooves 202 with the electrolyte-containing material 206 and the step of covering the filled electrolyte-containing material 206 with the oxygen gas-permeable membrane 207 are difficult to carry out in a semiconductor process, and therefore, are manually carried out chip by chip after the wafer 201 on which miniaturized oxygen electrodes have been formed is cut into chips forming respective oxygen electrodes. The manual operation is a serious obstacle to the realizing of a mass-production, and further, involves too much fluctuation in operation to obtain miniaturized oxygen electrodes having a stable or uniform performance.

Therefore, it has been desired to provide a structure of a miniaturized oxygen electrode and a production process thereof in which the filling of an electrolyte-containing material and the forming of an oxygen gas-permeable membrane can be carried out collectively or generally and uniformly, on a wafer as a whole, before the wafer is cut into chips.

The step of filling an electrolyte-containing material has the following problems.

The present inventors studied gels containing an aqueous solution of potassium chloride and polyelectrolytes and found that, because many of these are not photosensitive, the photolithography used in the semiconductor process cannot be actually applied to the filling of an electrolyte-containing material.

The electrolyte-containing material must be a liquid having a fluidity when it is filled in a groove, and the filled material must form a dense film after being dried. Also, whether or not the filled material contains water significantly affects the quality of an oxygen gas-permeable membrane applied on the filled material, and therefore, upon application for an oxygen gas-permeable membrane, the electrolyte-containing material is preferably dried. The water required for the measurement of the oxygen concentration is supplied as a water vapor through the gas-permeable membrane just before the measurement starts. The electrolyte-containing material need not contain water during the production of an oxygen electrode.

Screen printing is a preferred method of filling an electrolyte-containing material collectively in a number of miniaturized oxygen electrodes on a wafer. This screen printing generally uses an emulsion mask and a metal mask to define a printed pattern. An emulsion mask is prepared by applying a photosensitive resin in the form of an emulsion on a mesh of a stainless steel, etc. to provide a printing pattern. Some resins have a transparency which advantageously facilitates the fine alignment required when producing a miniaturized oxygen electrode because a wafer covered by a resin mask is visible through the resin. The emulsion mask, however, is very weak against water, as can be understood from the fact that the developing treatment of an emulsion is carried out by using water, and the printing of a water-containing substance is difficult. On the other hand, the metal mask is prepared by forming holes in a plate of a stainless steel, etc., and therefore, is strong against water. The metal mask, however, is disadvantageous for the fine alignment, because it does not have a transparency. Moreover, the metal mask occasionally provides a printing quality lower than that obtained by the emulsion mask, when using some kinds of printing inks.

The present inventors proposed a process in which an electrolyte-containing gel is applied by screen printing, i.e. calcium alginate gel, polyacrylamide gel, and agarose gel are printed, as disclosed in Japanese Unexamined Patent Publication (Kokai) No. 1-56,902. This process uses a metal mask to print an aqueous gel and cannot be advantageously used in the production of a miniaturized oxygen electrode, for the reasons mentioned above. Moreover, a strong film cannot be obtained because an oxygen gas-permeable membrane is formed on a wet gel.

Potassium chloride is generally used as the electrolyte of an oxygen electrode. Although potassium chloride is a superior electrolyte, it is not suitable for use in a miniaturized oxygen electrode because it has a drawback in that it is only soluble in water and that a filled aqueous solution becomes a white brittle powder when dried. The present inventors also proposed a polyelectrolyte, as disclosed in Japanese Unexamined Patent Publication (Kokai) No. 2-240,556. Although this has a good film forming property, the proposed polyelectrolyte is also soluble only in water, and is difficult to treat because it has a high polymerization degree and exhibits a high viscosity even as a dilute solution.

The step of forming an oxygen gas-permeable membrane has the following problems.

The gas-permeable membrane is made of silicone resin, fluororesin, or other electrically insulating material. The gas-permeable membrane is therefore formed not to cover the whole surface of a wafer but to have a pattern such that the component electrode ends or "pads" 204A and 205 for external electrical connection are exposed. The gas-permeable membrane is formed selectively in the predetermined wafer region other than the pad region to be exposed either by applying a resin only to the predetermined region or by first forming the gas-permeable membrane on the whole surface of a wafer and then removing the gas-permeable membrane in the pad region to be exposed.

A screen printing of a liquid resin is known as the former method, i.e., the selective application of a resin. This method has an advantage in that a single printing operation simultaneously effects both the application and the patterning of a resin, but the silicone resin used for forming a gas-permeable membrane is progressively cured by the water in the ambient air, and therefore, the viscosity of the resin varies during printing to cause a nonuniform printing, and in the worst case, a clogging of a printing stencil.

A lift-off process using a photoresist is known as the latter method, i.e., the formation and selective removal of a gas-permeable membrane. This process has an advantage in that the semiconductor process is advantageously applied and a complicated pattern can be easily obtained. This method, however, when applied in the production of a miniaturized oxygen electrode, provides a completely cured gas-permeable membrane having a high strength such that the membrane is difficult to peel or exfoliate selectively at the portion to be exposed, even by using an ultrasonic treatment. Thus, the lift-off process cannot be practically used in the production of a miniaturized oxygen electrode.

U.S. Pat. No. 4,062,750 to J. F. Butler discloses a thin film type electrochemical electrode formed on a silicon substrate, having a feature in that an electroconductive layer extends through the silicon substrate thickness so that a signal from a sensor disposed on one side of the substrate is taken out from the other side of the substrate. As this electrode does not have the pad portion of the present inventive electrode, a gas-permeable membrane may cover the whole surface and a patterning of the membrane for exposing the pad portion is not required. This electrode, however, requires a complicated production process, causing a problem in the practical application. The filling of an electrolyte is carried out by vacuum deposition, and although sodium chloride and potassium chloride can be vacuum deposited, many of the inorganic salts used as a buffering agent are deteriorated by dehydration and condensation when exposed to the heat associated with vacuum deposition. Therefore, even when a buffered electrolyte is obtained, the resulting pH will significantly deviate from an expected value and the obtained electrolyte composition must be very restricted, and thus this is not an optimum process. Moreover, problem arises when a single vacuum deposition apparatus is used for both depositing electrolytes and for depositing electrode metals, and therefore, individual deposition apparatuses must be provided for the respective depositions.

M. J. Madou et al. proposed a micro-electrochemical sensor, as disclosed in U.S. Pat. No. 4,874,500 and in AIChE SYMPOSIUM SERIES, No. 267, vol. 85, pp. 7–13 (1989). This sensor also has a feature in that an electroconductive layer extends through the silicon substrate thickness and a signal from a sensor disposed on one side of the substrate is taken out from the other side of the substrate, and therefore, has the same drawback as that of J. F. Butler. An electrolyte is filled in such a manner that an alcoholic solution of poly(hydroxyethylmathacrylate), etc. is painted on, the solvent is evaporated, an electrolyte solution is introduced to form a gel, and then dried. The conventional problem is apparently eliminated, because an electrolyte is introduced after a polymer is applied, but a crystal grows when a potassium chloride solution is evaporated. When the amount of potassium chloride is small, the grown crystal is enclosed with the polymer, but when the amount is large, a number of large crystals appear, which may not be supported by the polymer. On the other hand, the amount of an electrolyte must be as large as possible, because the service life of an oxygen electrode is affected by the electrolyte amount contained therein. Thus, the restricted amount of electrolyte reduces the service life of an oxygen electrode.

SUMMARY OF THE INVENTION

The object of the present invention is to provide a miniaturized oxygen electrode which can be mass-produced at a high efficiency by collectively and uniformly processing a substrate as a whole, a production process thereof, and an electrolyte composition able to be advantageously used therefor.

To achieve the above object according to the first aspect of the present invention, there is provided an electrolyte composition for screen printing, comprising:

an organic solvent;

an inorganic salt in the form of a fine powder able to pass through a screen printing mesh, the salt powder being dispersed in the organic solvent; and polyvinyl pyrrolidone dissolved in the organic solvent.

The electrolyte composition is screen-printed to form an electrolyte-containing material on a substrate.

The inorganic salt is preferably selected from potassium chloride and sodium chloride.

The inorganic salt used as an electrolyte must be in the form of a fine powder which can pass through the screen printing mesh, for example, in the form of a fine particle having a diameter not larger than 50 μm.

The organic solvent used in the present invention is preferably an alcohol such as butanol, pentanol, or hexanol.

The present inventive electrolyte composition is prepared by dispersing an inorganic salt such as potassium chloride, which is a superior electrolyte, in the form of a fine particle adapted for screen printing, in a high molecule polymer dissolved in an organic solvent. The present invention uses polyvinyl pyrrolidone as the high molecule polymer. An inorganic salt such as potassium chloride in the form of a fine particle may be prepared either by pulverizing a solid material or by pouring an aqueous solution containing an inorganic salt in saturation or in a high concentration near saturation into an organic solvent such as alcohol and acetone, which can be mixed with water in any proportion, to precipitate fine particles. Either method provides a powder of fine particles having a uniform size.

The present inventive electrolyte composition may further comprise a buffering agent, to ensure a constant pH (hydrogen ion concentration) of the electrolyte. The buffering agent is a salt exhibiting a buffering effect, such as phosphate, acetate, borate, citrate, phthalate, tetraborate, glycine salt, and tris(hydroxymethyl)-aminomethane salt, and is used in the form of a fine powder like the potassium chloride powder.

According to the second aspect of the present invention, there is also provided a miniaturized oxygen electrode comprising:

an electrically insulating substrate;

an electrolyte-containing material disposed on the substrate;

a set of component electrodes in contact with the electrolyte-containing material and disposed on the substrate; and an oxygen gas-permeable membrane covering the electrolyte-containing material;

the electrolyte-containing material being formed by screen-printing on the substrate the electrolyte composition according to the first aspect of the present invention.

According to the third aspect of the present invention, there is provided a process of producing a miniaturized oxygen electrode, comprising the steps of:

preparing an electrically insulating substrate;

forming an electrolyte-containing material on the substrate; and forming on the substrate a set of component electrodes in contact with the electrolyte-containing material;

forming an oxygen gas-permeable membrane covering the electrolyte-containing material;

the forming of the electrolyte-containing material being carried out by screen-printing on the substrate the electrolyte composition according to the first aspect of the present invention.

According to the second and third aspects of the present invention, a fine powder of an inorganic salt, polyvinyl pyrrolidone, and an organic solvent are blended to form an electrolyte composition in the form of a paste, which is then applied to a substrate at predetermined portions collectively by screen printing. The printed electrolyte composition, when dried, forms a dense film such that an oxygen gas-permeable membrane can be properly formed thereon.

According to the fourth aspect of the present invention, there is provided a miniaturized oxygen electrode comprising:

an electrically insulating substrate;

an electrolyte-containing material disposed on the substrate;

a set of component electrodes disposed on the substrate, each having an end in contact with the electrolyte-containing material and an end for external electrical connection; and an oxygen gas-permeable membrane covering the substrate in a portion containing the electrolyte-containing material;

the oxygen gas-permeable membrane being removed from the substrate in a region containing the end for external electrical connection, by removing a removable cover film interposed between the substrate and the oxygen gas-permeable membrane.

According to the fifth aspect of the present invention, there is provided a process for producing a miniaturized oxygen electrode, comprising the steps of:

preparing an electrically insulating substrate;

forming an electrolyte-containing material on the substrate;

forming on the substrate a set of component electrodes each having an end in contact with the electrolyte-containing material and an end for external electrical connection; and forming a removable cover film on the substrate in a region to be exposed in the following removing step, the region containing the component electrode end for external electrical connection;

forming an oxygen gas-permeable membrane covering the substrate surface including the region of the removable cover film; and removing the oxygen gas-permeable membrane by peeling the removable cover film away from the substrate surface, to expose the to-be-exposed region of the substrate and thereby shape the oxygen gas-permeable membrane to a predetermined pattern.

The process according to the fifth aspect of the present invention preferably comprises the steps of:

screen-printing a thermosetting resin onto the to-be-exposed region of the substrate;

heating the resin to cure the resin to form a resin film as the removable cover film;

forming the oxygen gas-permeable membrane covering the substrate surface including the region of the resin film;

peeling the resin film to expose the to-be-exposed region, and thereby shape the oxygen gas-permeable membrane to a predetermined pattern.

According to the fourth and the fifth aspects of the present invention, an oxygen gas-permeable membrane is formed selectively or patterned to cover the necessary region of the substrate surface by first covering a region of substrate to be exposed with a removable cover film, applying a resin for forming an oxygen gas-permeable membrane onto the whole surface of the substrate by spin coating, and then peeling or exfoliating the removable cover film to thereby remove the oxygen gas-permeable membrane together with the cover film in the region of substrate to be exposed. The present invention uses, as the material of the removable cover film, a thermosetting resin, a solution of polyvinylchloride in an organic solvent, or other resins. Such resins are applied to the predetermined region of a substrate by screen printing, and then cured by heating or drying to form a removable cover film.

The electrically insulating substrate, on which the present inventive miniaturized oxygen electrode is formed, may be an electrically insulating substrate having a flatness and a smoothness sufficient for forming a miniaturized oxygen electrode by using the semiconductor process. A silicon wafer is most advantageously used as the insulating substrate, from the viewpoint of the application of the production process of silicon semiconductors currently most generally used.

The present invention may be directly applied to miniaturized oxygen electrodes formed on insulating substrates other than the silicon wafer. Namely, a miniaturized oxygen electrode is produced by using a flat substrate of an electrically insulating substance such as glass, quartz and plastics, in such a manner that a component electrode pattern is formed on the substrate, an electrolyte-containing material is filled in the oxygen sensing site by screen printing an electrolyte composition of the present invention, and then an oxygen gas-permeable membrane is selectively formed or patterned by the steps including forming a removable cover film by screen-printing a thermosetting resin, etc., on the pad portion, i.e., the region of the substrate including the component electrode end for external electrical connection. It will be easily understood that, even in this case, the present invention also provides an advantage in that a number of miniaturized oxygen electrodes are formed collectively at one time on the whole region of an integral substrate.

According to the present invention, the screen-printed electrolyte composition contains a fine powder of an inorganic salt or an electrolyte not dissolved but dispersed in an organic solvent, and therefore, the inorganic salt, even when dried, does not form a brittle crystal but remains a fine powder, and this enables an electrolyte-containing material in the form of a dense solid material to be formed. The thus obtained electrolyte-containing material is essentially composed of the inorganic salt and polyvinyl pyrrolidone. Upon operating a miniaturized oxygen electrode, water is introduced into the electrolyte-containing material. Both the inorganic salt and polyvinyl pyrrolidone are water-soluble and completely dissolved in the introduced water, and thus the present inventive electrolyte-containing material satisfies the requirement for a miniaturized oxygen electrode that it remains in a solid state during the formation of an oxygen gas-permeable membrane and forms an aqueous solution when the miniaturized oxygen electrode is operated.

Potassium chloride and sodium chloride are superior electrolytes and can be advantageously used as the inorganic salt according to the present invention, to obtain the best performance of a miniaturized oxygen electrode.

The addition of a salt having a pH buffering effect, such as phosphate, to the present inventive electrolyte composition ensures that the electrolyte has a constant pH. As the electrochemical reaction in the oxygen electrode depends on the pH value, the constant pH improves the stability of the oxygen electrode performance.

The miniaturized oxygen electrode according to the present invention is produced by filling an electrolyte composition containing an inorganic salt as an electrolyte in the form of a fine powder, collectively in all of the predetermined portions of a substrate, by screen printing, to thereby ensure a uniform filling operation and a high productivity.

The process of producing a miniaturized oxygen electrode according to the present invention fills an electrolyte composition containing an inorganic salt as an electrolyte in the form of a fine powder, collectively in all of the predetermined portions of a substrate by screen printing, and thereby ensures a uniform filling operation and mass-production of a miniaturized oxygen electrode even when the filled portion has a complicated shape. The present inventive production process can also advantageously cope with any increase in the number of filling portions associated with an enlargement of the substrate size.

The miniaturized oxygen electrode according to the present invention ensures a high productivity even when the oxygen gas-permeable membrane and the exposed portion have a complicated shape, because the oxygen gas-permeable membrane is patterned (or selectively formed) by removing a cover film formed in a predetermined shape. The oxygen gas-permeable membrane is applied collectively on the entire substrate surface by spin-coating, and thereby a high productivity is ensured and an oxygen gas-permeable membrane having a uniform thickness over the entire substrate surface is formed.

The miniaturized oxygen electrode according to the present invention can be produced at a high productivity by effectively forming an oxygen gas-permeable membrane having a uniform thickness over the entire substrate surface, i.e., by first covering a substrate region to be exposed with a removable cover film, forming an oxygen gas-permeable membrane collectively on the entire substrate surface, and then peeling or exfoliating the removable cover film to selectively form or pattern the oxygen gas-permeable membrane.

The process according to the present invention can easily cope with a complicated pattern of oxygen gas-permeable membrane and with any increase in the number of portions to be exposed, because an oxygen gas-permeable membrane is patterned through the steps of: applying a thermosetting resin of a resin dissolved in an organic solvent to the to-be-exposed portions by screen printing; curing the applied resin by heating or drying to form a removable cover film; and then peeling or exfoliating the removable cover film.

FIGS. 12(A) and 12(B) show a miniaturized oxygen electrode according to the present invention. A miniaturized oxygen electrode 1 shown in FIG. 12(A) is one cut from a number of chips formed simultaneously or collectively on a single silicon wafer 13 shown in FIG. 12(B). A cathode 2 and an anode 3 are formed on an electrically insulating substrate, composed of a silicon wafer 13 with silicon oxide films 21 formed on both sides, and are connected to each other via an electrolyte-containing material which becomes an electrolyte solution when water is introduced therein. The cathode 2 and the anode 3 are formed or patterned by etching a metal film having an uppermost silver film. The metal film forms external connection terminals (pads) 7 and 8, leads 2A and 3A, and the component electrodes 2 and 3. The surface of the miniaturized oxygen electrode 1 is covered with a photoresist or other hydrophobic film 10 except for a pad region 12 in which the pads are exposed. The hydrophobic film 10 also has openings 5 and 6, through which the cathode 2 and the anode 3 are connected to the electrolyte-containing material 4, respectively. A substantial oxygen sensing site is provided by the opening 5 through which the cathode 2 and the electrolyte-containing material 4 are connected to each other. A gas-permeable membrane, not shown, covers the entire surface of the miniaturized oxygen electrode 1 except for the pad region 12.

The miniaturized oxygen electrode 1 shown in FIG. 12(A) is operated by applying a negative potential to the cathode 2 relative to the anode 3. By maintaining this potential and holding the oxygen sensing site immersed in a buffering solution, oxygen dissolved in the solution penetrates the gas-permeable membrane to reach a working electrode or cathode and is reduced there. The value of a current generated by this reduction reaction is measured to evaluate the dissolved oxygen concentration.

Japanese Unexamined Patent Publication (Kokai) No. 4-125462 disclosed a miniaturized oxygen electrode of this type, which was developed, by the present inventors, by the combined use of anisotropic etching and an anode-bonding process to facilitate industrial manufacture and to provide improved performance.

Miniaturized oxygen electrodes of this type need a silicon or glass substrate and use a lithography process, and therefore, it is impossible to realize a low price not more than 100 yen per chip which is comparable with that of testing paper, even if the equipment and other production conditions are optimized and if there is a demand of several tens of millions of electrodes per year or more. To realize a reduced electrode price, the present inventors also developed a miniaturized oxygen electrode having a plastic substrate, a paper patch with an electrolyte solution infiltrated therein, and a gas-permeable membrane adhered to an oxygen sensing site (Japanese Unexamined Patent Publication (Kokai) No. 6-34596).

Although smaller and less expensive than the conventional Clark type oxygen electrode, the miniaturized oxygen electrode has a problem in that it does not provide sufficient stability for long-term continuous operation. For example, when the miniaturized oxygen electrode is continuously operated for a long time with the oxygen sensing site immersed in an aqueous solution saturated with air, the measured current value either continuously rises or fluctuates widely, even though it should remain constant for a constant oxygen concentration.

A further object of the present invention is to provide a miniaturized oxygen electrode having an improved stability during long-term continuous operation.

To achieve the above object according to the present invention, there is provided a miniaturized oxygen electrode comprising:

an electrically insulating substrate;

an electrolyte-containing material disposed on the substrate to form an electrolyte solution when water is introduced thereto;

a set of component electrodes disposed on the substrate and connected with each other via the electrolyte-containing material;

a gas-permeable membrane covering the electrolyte-containing material;

the set of component electrodes including a cathode on which a reduction reaction of oxygen occurs and an anode as a counterpart of the cathode;

the electrolyte-containing material being composed of a first layer and a second layer which are mutually connected, the first layer containing no electrolytes and being connected to the cathode and the second layer containing an electrolyte and being not connected from the cathode, the mutual connection of the first layer and the second layer being effected so that, during the water introduction and a subsequent holding, the electrolyte of the second layer diffuses to the first layer to form a single electrolyte solution layer.

The reduction reaction of oxygen of the cathode has generally two phases. In the first phase oxygen is once reduced to hydrogen peroxide by two-electron transfer and in the second phase, it is further reduced to OH⁻ by two-electron transfer. These reactions proceed in different manners depending not only on the metal used as the cathode but also on the surface conditions of the cathode (the degree of deterioration and contamination). In this micro sensor, a silver/silver halide (particularly, silver/silver chloride) electrode is used as a reference electrode (i.e., anode). The silver chloride, however, is dissolved during operation of the sensor and is reduced on the cathode to precipitate silver. To avoid this phenomenon and keep the cathode surface unchanged during operation, silver is used to form the cathode as mentioned above. However, a silver cathode is particularly prone to deteriorate. When cathode deterioration occurs during the manufacture or handling of miniaturized oxygen electrodes, the large amount of the resultant intermediate products preclude stable measurement.

The present inventors found that the cathode deterioration precludes the stable operation of miniaturized oxygen electrodes, and further, that the cathode deterioration occurs during production of the miniaturized oxygen electrode.

As shown in FIG. 12(A), a gas-permeable membrane 10 (not shown) is overlaid on the electrolyte-containing material 4 kept in contact with the silver cathode 2. The gas-permeable membrane 10 includes a photoresist layer, which need be prebaked and postbaked, for example, at about 80° C. and at about 150° C., respectively. The present inventors found that the electrolyte of the electrolyte-containing material 4 reacts with and deteriorates the silver cathode 2 during the baking processes.

The present inventors found that the cathode deterioration is also caused during water introduction into the miniaturized oxygen electrode.

To operate a miniaturized oxygen electrode, water must be introduced into an electrolyte-containing material 4 to form an electrolyte solution. Usually, water is introduced either by boiling in water or by exposure to a high temperature water vapor at about 120° C., and takes about one hour. During this process of water introduction, the electrolyte of an electrolyte-containing material reacts with and deteriorates the silver cathode.

According to the present invention, the cathode deterioration by an electrolyte does not occur during production and during water introduction, because the electrolyte-containing material 4 is composed of a first layer and a second layer which are mutually connected, the first layer containing no electrolytes and being connected to the cathode and the second layer containing an electrolyte and being not connected from the cathode, the mutual connection of the first layer and the second layer being effected so that, during the water introduction and a subsequent holding, the electrolyte in the second layer diffuses to the first layer to form a single electrolyte solution layer.

BRIEF DESCRIPTION OF THE DRAWINGS

FIGS. 8(a) through (c) show a three-pole miniaturized oxygen electrode;

DESCRIPTION OF THE PREFERRED EMBODIMENTS

Example 1

Figure 1:
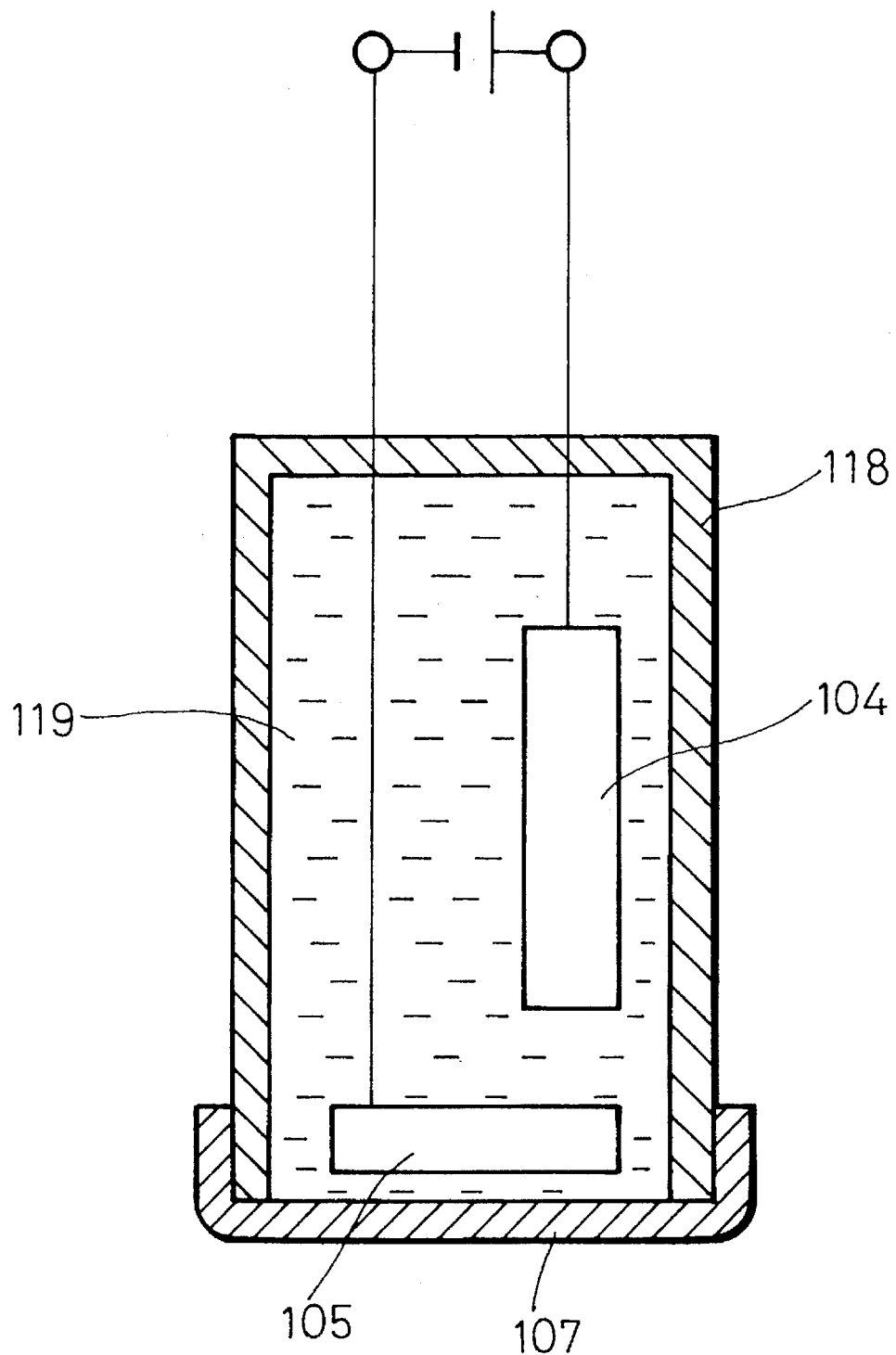
FIG. 1 shows the essential arrangement of a conventional oxygen electrode, in Section view.
Figure 2A:
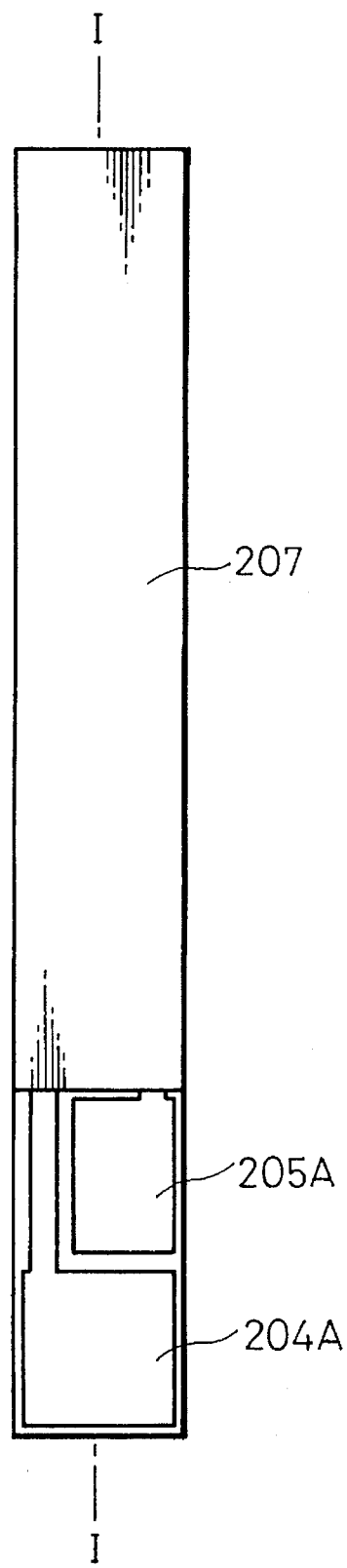
FIGS. 2(a) through (c) show a miniaturized oxygen electrode in plan view (a, b) and sectional view (c)
Figure 2B:
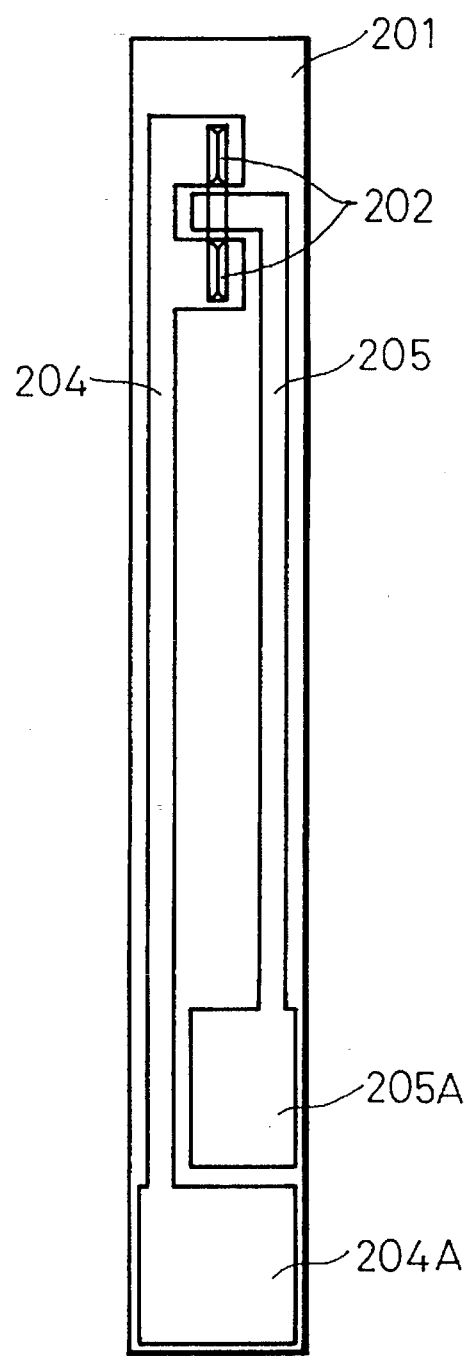
Figure 2C:
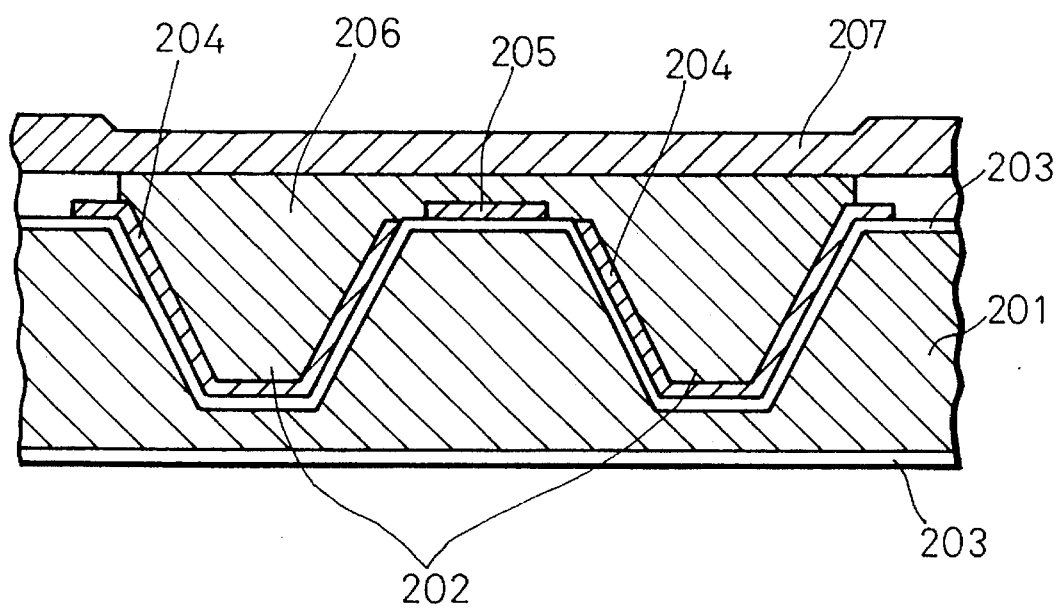
Figure 3A:
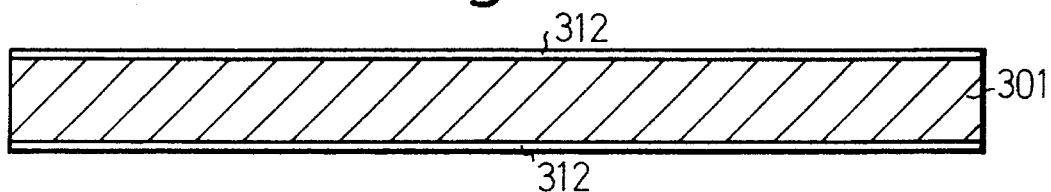
FIGS. 3(a) through (n) show a process sequence according to the present invention, in sectional and plan views.
Figure 3B:
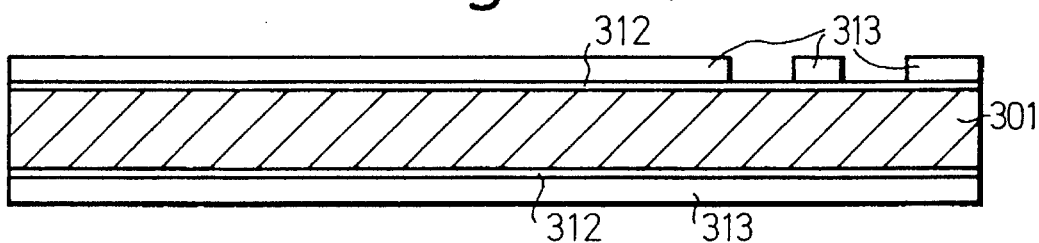
Figure 3C:
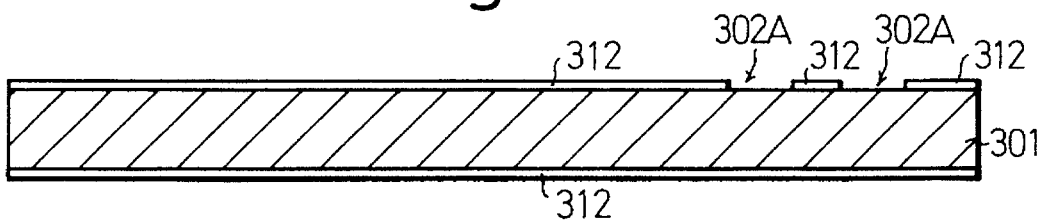
Figure 3D:
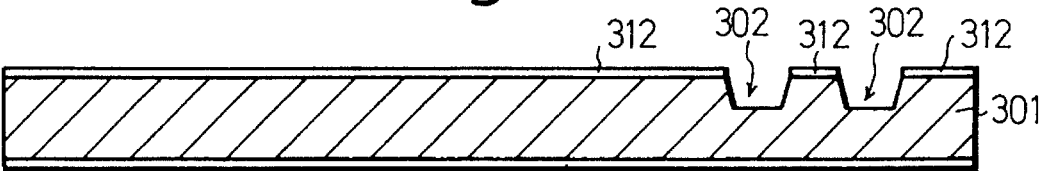
Figure 3E:
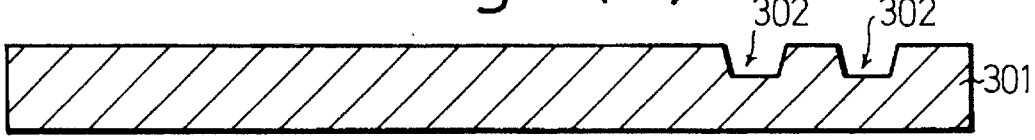
Figure 3F:
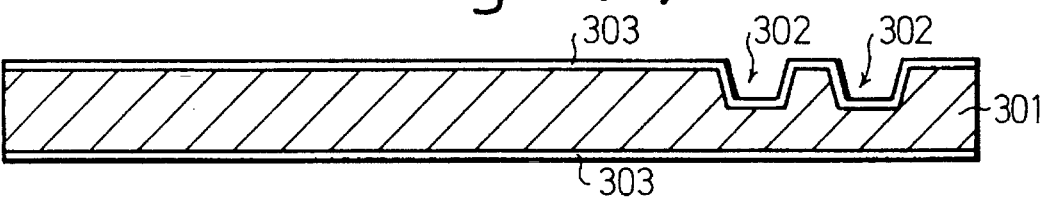
Figure 3:
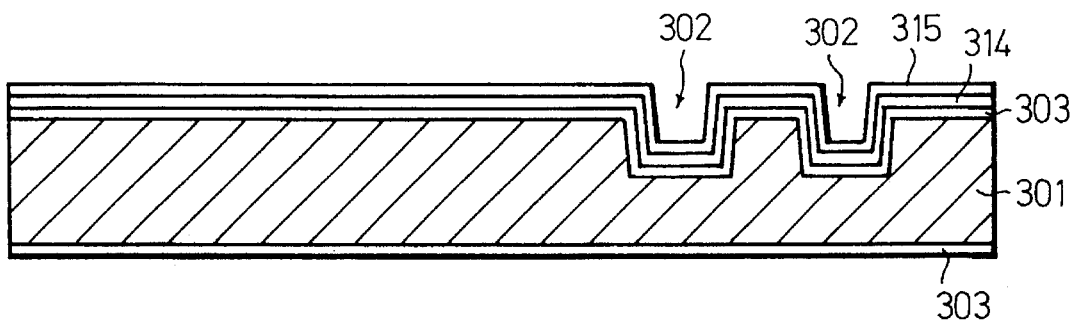
Figure 3:
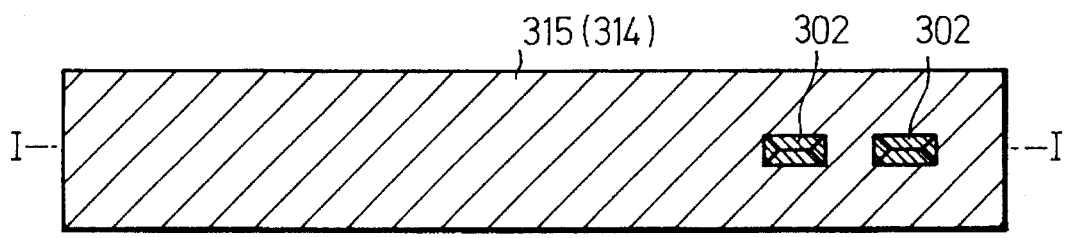
Figure 3:
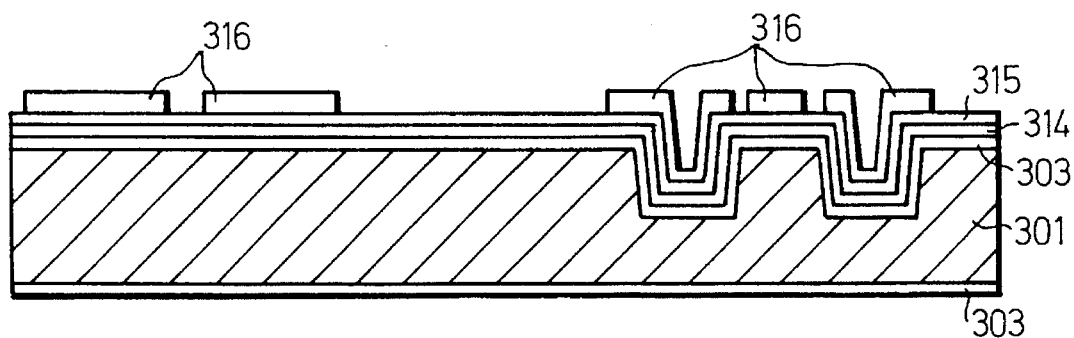
Figure 3:
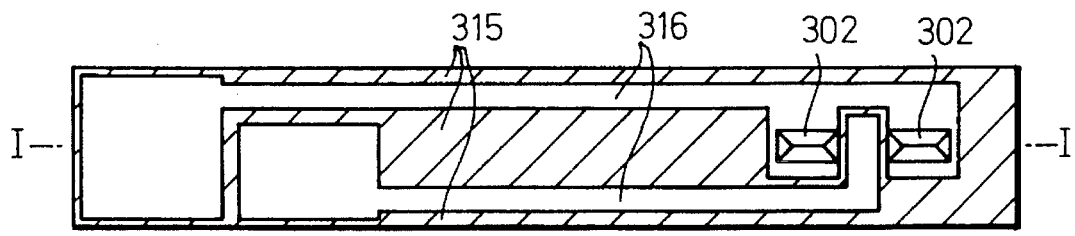
Figure 3:
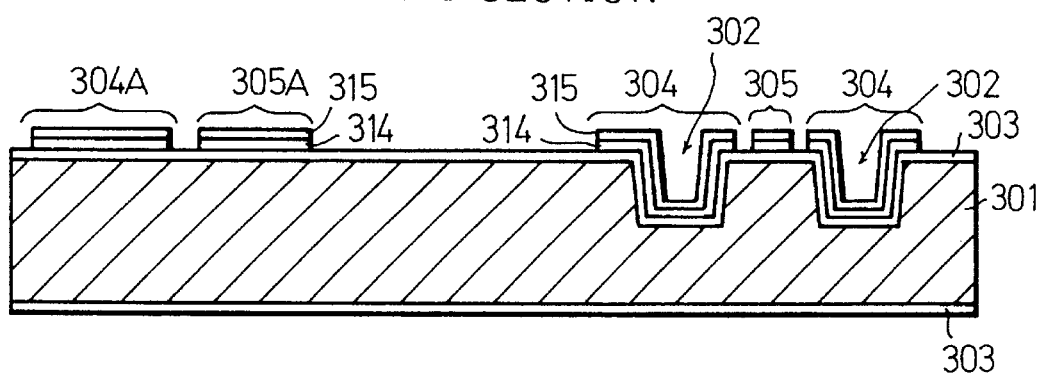
Figure 3:
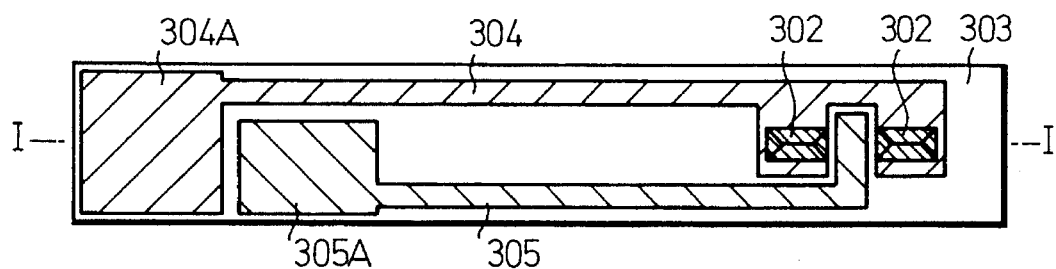
Figure 3:
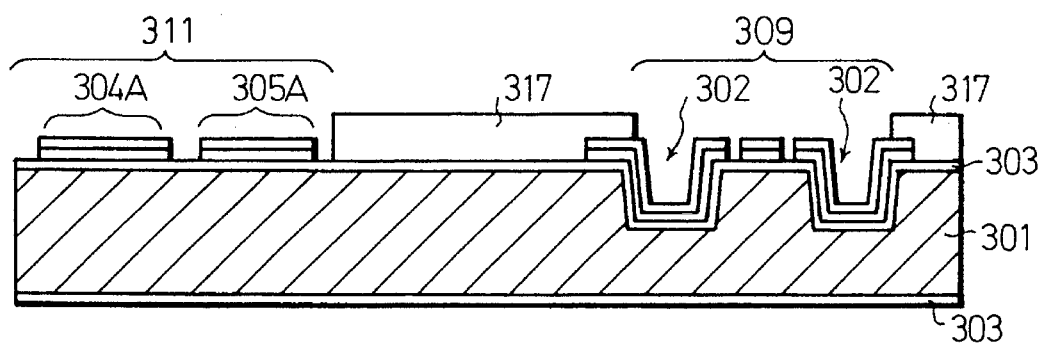
Figure 3:
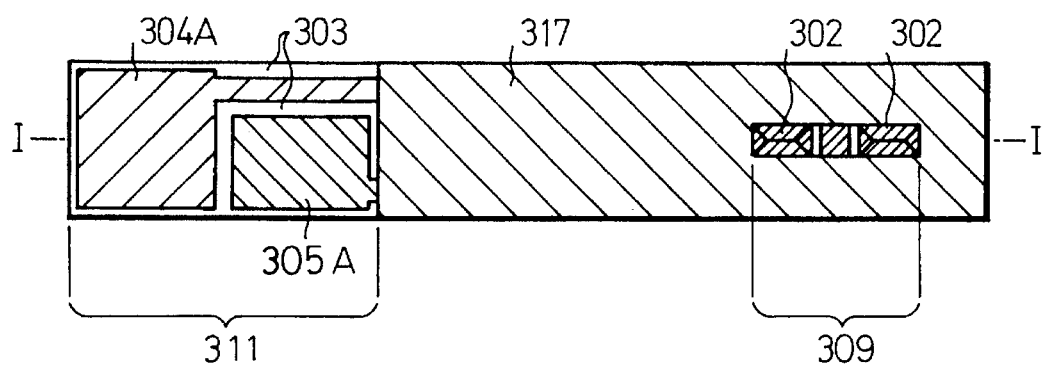
Figure 3:
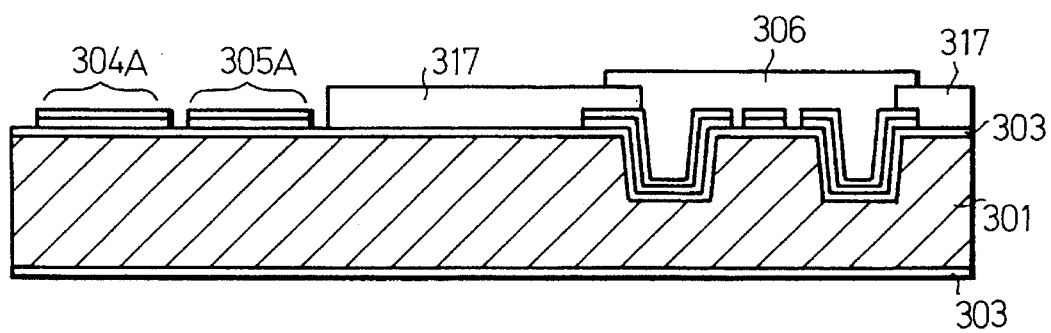
Figure 3:
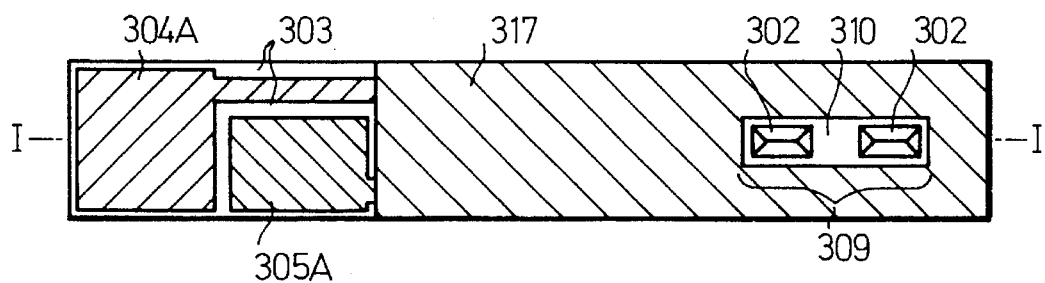
Figure 3:
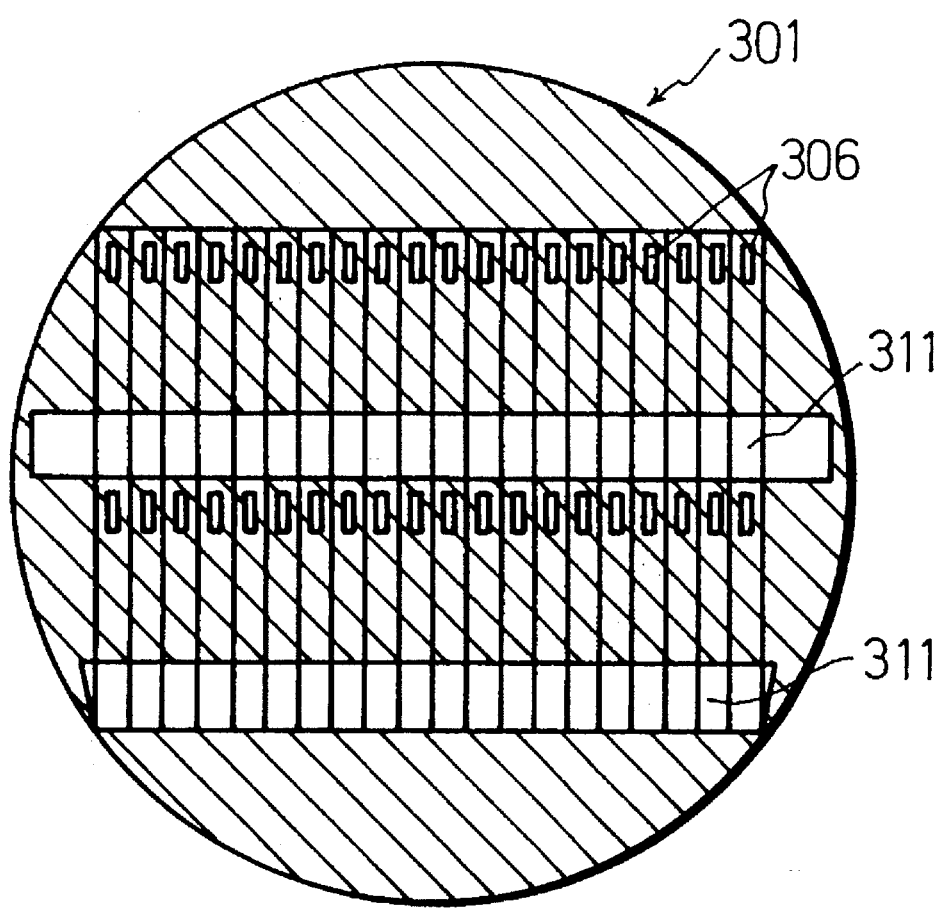
Figure 3:
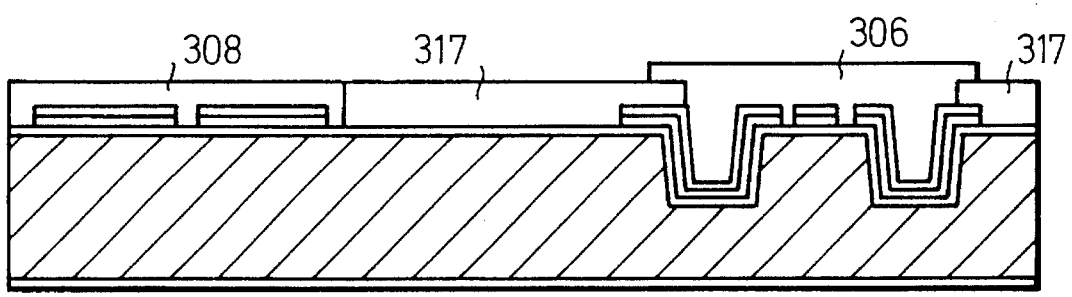
Figure 3:
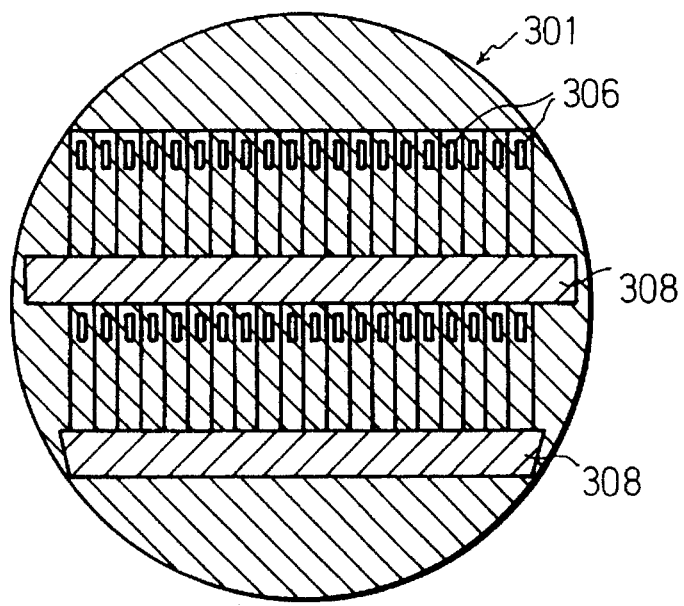
Figure 3:
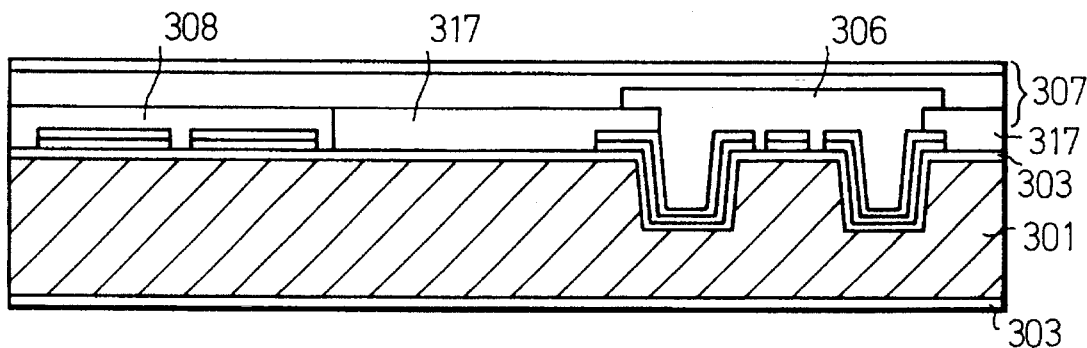
Figure 3:
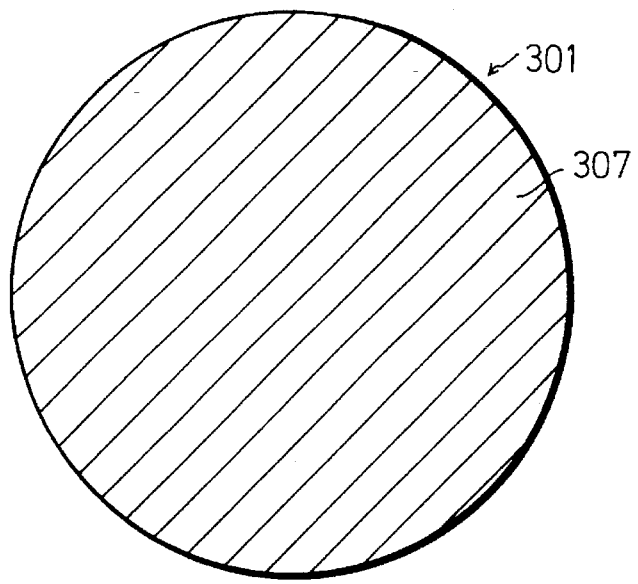
Figure 3:
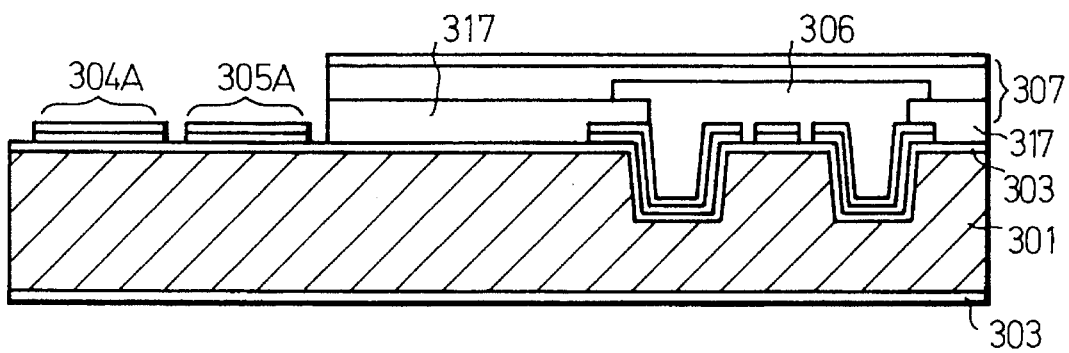
Figure 3:
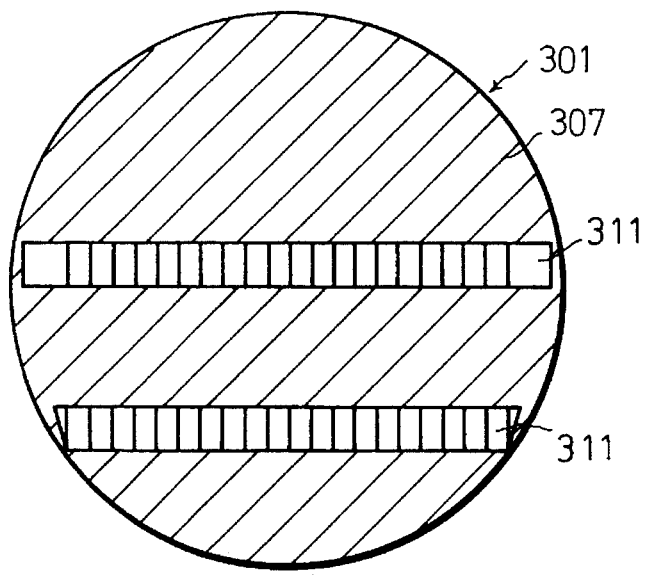

Referring to FIG. 3, a process sequence for producing a miniaturized oxygen electrode according to the present invention by using a silicon wafer will be described below. Although the sequence is described for the case in which a miniaturized oxygen electrode is formed on a 2-inch silicon wafer, for simplicity, essentially the same process sequence can be also used for a larger wafer. The Figures depict the wafer in which the corresponding process step is completed.

Step 1: Cleaning Wafer

A 2-inch silicon wafer 301 (400 µm thick, (100) plane) was thoroughly cleaned with a mixed solution of hydrogen peroxide and ammonia and with a concentrated nitric acid.

Step 2: Forming $SiO_2$ Layer (FIG. 3(a))

The wafer 301 was wet-thermally oxidized at 1000° C. for 200 min. to form a 0.8 µm thick $SiO_2$ layer 312 on both sides of the wafer. The $SiO_2$ layer 312 is to be patterned in the following step 4 and used as a mask when anisotropically etching the silicon wafer in the following step 5.

Step 3: Forming Resist Pattern (FIG. 3(b))

A negative-type photoresist (Tokyo Ohka Kogyo Co., Ltd., OMR-83, viscosity 60 cP) was applied on the entire upper surface of the wafer, prebaked at 80° C. for 30 min. and was subjected to a photolithography treatment to form a resist pattern 313. The resist pattern 313 covers the upper surface of the wafer 301 except for a region 302A at which grooves 302 (FIG. 3(d)) for receiving an electrolyte-containing material are to be formed in the following step 5. The resist pattern 313 serves as a mask upon etching the $SiO_2$ layer 312 in the following step 4. The same photoresist was applied on the lower surface of the wafer 301, which was then baked at 150° C. for 30 min.

Step 4: Etching $SiO_2$ Layer (FIG. 3(c))

The wafer 301 was immersed in en etchant for $SiO_2$ (50%HF/1 ml+$NH_4F$/6 ml) to partially remove the $SiO_2$ layer 312 in the portion 302A not covered with the photoresist 313. The wafer 301 was then immersed in a mixed solution of connected sulfuric acid and hydrogen peroxide, to remove the photoresist 313.

Step 5: Anisotropically Etching Silicon Wafer (FIG. 3(d))

The wafer 301 was immersed in an etchant for silicon (35% KOH) at 80° C. to anisotropically etch the silicon wafer 301 by using the $SiO_2$ layer as a mask, and thereby forming two 300 µm deep grooves 302 for receiving an electrolyte-containing material. After the anisotropic etching was finished, the wafer 301 was cleaned with pure water.

Step 6: Removing $SiO_2$ Layer (FIG. 3(e))

Subsequent to the water cleaning, the $SiO_2$ layer 312 was removed by the same operation as that performed in Step 4.

Step 7: Forming $SiO_2$ Layer (FIG. 3(f))

The same operations as performed in Steps 1 and 2 were carried out to effect a thermal oxidation of the wafer 301, and thereby form a 0.8 µm thick $SiO_2$ layer 303 on the entirety of both sides of the wafer 301. The thus-formed $SiO_2$ layer 303 functions as an insulating layer of a miniaturized oxygen electrode or the final product.

Step 8: Forming Thin Layers of Chromium and Silver (FIGS. 3(g1), 3(g2))

A 400 Å thick chromium thin 314 and a 4000 Å thick silver thin layer 315 overlying on the chromium layer 314, were formed on the entire upper surface of the wafer 301 by vacuum deposition. The silver thin layer 315 is an electroconductive layer composing the substantial portion of component electrodes (anode and cathode) and the chromium thin layer 314 is a ground layer for ensuring an adhesion of the silver thin layer 315 to the SiO$_2$ insulating layer 303 formed on the wafer 301.

Step 9: Forming Photoresist Pattern FIGS. 3(*h*1), 3(*h*2))

This step provides a photoresist pattern 316 to be used as a mask in the following Steps 10 and 11, in which the silver thin layer 315 and the chromium thin layer 314 are etched to thereby effect a patterning of component electrodes (anode and cathode) of a miniaturized oxygen electrode.

A positive-type photoresist (Tokyo Ohka Kogyo Co., Ltd., OFPR-800, viscosity 20 cP or OFPR-5000, viscosity 50 cP) was dropped on the wafer 301 to uniformly cover the wafer 301. The photoresist is preferably dropped in an amount such that it spreads just to the wafer circumferential edge. The wafer 301 was prebaked at 80° C. for 30 min.

The wafer 301 was pattern-aligned with a glass mask by a mask aligner, exposed to light, and developed to form a photoresist pattern 316. The exposure and development cycle was repeated to ensure a complete exposure of the positive-type photoresist layer, which is too thick to complete the exposure over the thickness at one time.

Step 10: Etching Thin Layers of Silver and Chromium (FIGS. 3(*i*1) and 3(*i*2))

The wafer 301 was immersed in an etchant for silver (NH$_3$ water/1 ml+H$_2$O$_2$/1 ml+water/20 ml) to remove a bare portion of the silver layer, and thereby form the substantial portion of component electrodes.

The wafer was then immersed in an etchant for chromium (NaOH/0.5 g+K$_3$Fe(CN)$_6$/1 g+water/4 ml) to remove a bare portion of the chromium layer 314.

Step 11: Forming Photoresist Pattern (FIG. 3(*j*1) and 3(*j*2)

This step provides a photoresist pattern 317 for defining the oxygen sensing site of a miniaturized oxygen electrode.

A layer 317 of a negative-type photoresist (Tokyo Ohka Kogyo Co., Ltd., OMR-83, viscosity 60 cP) was formed on the wafer 301 to cover the wafer surface in the portion other than a region 309 of the oxygen sensing site (two grooves and a flat plateau therebetween) and a pad region 311, at which the pad portions 304A and 305A of component electrodes 304 and 305 are to be formed. This is performed by applying the photoresist to the wafer surface, prebaking the wafer at 80° C. for 30 min, and exposing to light and developing the photoresist layer. Thereafter, the photoresist layer was postbaked at 150° C. for 30 min.

Step 12: Screen-Printing Electrolyt Composition (FIGS. 3(*k*1), 3(*k*2) and 3(*k*3)

An electrolyte composition was screen-printed at the oxygen sensing site 309 (two grooves and a flat plateau therebetween) defined by the photoresist 317, to form an electrolyte-containing material 306. The preparation of the electrolyte used will be described later.

Step 13: Forming Pad Region Cover Film (FIGS. 3(*l*1) and 3(*l*2))

A thermosetting release coating (Fujikura Kasei Co. XB-801) was screen-printed at the pad region 311 at a thickness of 100 μm and cured by heating at 150° C. for 10 min. to form a removable cover film 308.

Step 14: Forming Oxygen Gas-Permeable Membrane (FIGS. 3(*m*1) and 3(*m*2))

An oxygen gas-permeable membrane 307 having a double-layered structure was formed on the wafer 301 to entirely cover the upper surface of the wafer 301. The lower layer of the membrane 307 was first formed by applying a negative-type photoresist (Tokyo Ohka Kogyo Co., Ltd., OMR-83, viscosity 100 cP) to the wafer 301 by spin coating, prebaking at 80° C. for 30 min., exposing the entire wafer surface to light and developing, and postbaking at 150° C. for 30 min. The upper layer of the membrane 307 was then formed by applying a silicone resin (Toray-Dow Corning Silicone Co. SE9176) to the wafer 301 by spin coating and curing the coated resin by heating at 70° C. for 30 min. in an oven moistened by water contained in a Petri dish or a beaker placed in the oven.

Step 15: Exposing Pads (FIGS. 3(*n*1) and 3(*n*2)

The cover film 308 formed on the pad region 311 was peeled with a pincette to selectively remove the oxygen gas-permeable membrane in that region, and thereby expose the pads 304A and 305A of a miniaturized oxygen electrode.

Step 16: Separating Miniaturized Oxygen Electrodes

A number of miniaturized oxygen electrodes were collectively formed on the wafer 301 at one time by the preceding Steps 1 through 15 and were cut into chips by a dicing saw. The shown example provides forty chips of miniaturized oxygen electrodes at one time.

Example 2

Miniaturized oxygen electrodes were produced by the same process sequence as that of Example 1, except that Step 13 of forming a pad region cover film was modified as follows:

Step 13': Forming Pad Region Cover Film (Modified)

Polyvinylchloride resin dissolved in tetrahydrofuran was screen-printed at the pad region 311 at a thickness of 50 μm and cured by heating at 70° C. to form a cover film 308.

The electrolyte composition according to the present invention used in Step 12 of Examples 1 and 2 was prepared in the following manner.

Preparation Procedure 1: Providing Fine Powder of Inorganic Salt

Fine particles of potassium chloride or sodium chloride were formed by either of the following procedures (a) and (b):

(a) A solid material of potassium chloride or sodium chloride was pulverized to fine particles having a diameter of 10 μm or less by a pulverizer (Fritsch Co. Type P-5).

(b) A saturated aqueous solution of potassium chloride or sodium chloride was prepared. The solution was poured into an organic solvent such as ethanol, propanol, or acetone of an amount of ten times the solution, through a Teflon* ball filter (Iuchiseieido Co., pore diameter 10 μm). The organic solvent was thoroughly agitated by a stirrer during the pouring. This provided a precipitation of fine particles of inorganic salt, which was collected by a glas filter, washed two or three times with a fresh organic solvent of the same kind, and dried to obtain fine particles having a diameter of 10 μm or less.

(*) "Teflon": trademark of Du Pont Co. for polytetrafluoroethylene (PTFE)

Preparation Procedure 2: Blending Electrolyte Composition

The above-obtained fine particles of inorganic salt, polyvinyl pyrrolidone, and an organic solvent were blended to form an electrolyte composition in the form of a paste. The following is an example of the thus-blended composition.

| Electrolyte Composition: Case 1 | |
| --- | --- |
| Potassium chloride fine particle | 0.25 g |
| Polyvinyl pyrrolidone | 1 g |
| Pentanol | 5 g |

The blending may be carried out in a manner such that the electrolyte composition contains 30 to 70% of a solid part and the remainder of an organic solvent, the solid part containing 50 to 90% of an inorganic salt. The following is an example of the thus-blended composition.

| Electrolyte Composition: Case 2 | |
| --- | --- |
| Potassium chloride fine particle | 4 g |
| Polyvinyl pyrrolidone | 1 g |
| Pentanol | 5 g |

According to preferred embodiment of the present invention, an electrolyte composition further comprises a salt having a pH-buffering effect. Although a phosphate was added in the following case, the buffering agent used in the present invention may be selected from the group consisting of phosphates, accetates, borates, citrates, phthalates, tetraborates, glycine salts, and tris(hydroxymethyl)aminomethane salts.

An electrolyte composition with an addition of a phosphate as a buffering agent may be prepared in the following manner, for example.

Preparation Procedure 1: Providing Fine Powder of Inorganic Salt

Fine particles of potassium chloride or sodium chloride were formed by either of the following procedures (a) and (b):

(a) 74.55 g of potassium chloride and 8.71 g of dipotassium hydrogen phosphate were weighed and pulverized to particles having a diameter of 10 μm or less by a pulverizer (Fritsch Co., Type P-5).

(b) 74.55 g of potassium chloride and 8.71 g of dipotassium hydrogen phosphate were weighed and dissolved in 230 ml of water. The aqueous solution was poured into an amount of ethanol ten times the amount of the solution, through a Teflon ball filter (Iuchiseieido Co., pore diameter 10 μm). The ethanol was thoroughly agitated by a stirrer during the pouring. This resulted in a precipitation of fine particles of inorganic salt, which was then collected by a glass filter, washed with a fresh ethanol two or three times, and dried to obtain fine particles having a diameter of 10 μm or less.

The fine particles of potassium chloride or sodium chloride and the fine particles of phosphate or a buffering agent may be separately prepared. For example, when a concentrated aqueous solution of potassium chloride or sodium chloride is formed, an aqueous solution of potassium dihydrogen phosphate and sodium dihydrogen phosphate (4:6 in molar ratio) can be separately formed. Both solutions are preferably in a saturation state, which provides a greater amount of fine particles, i.e., a high efficiency. Note that the weighed phosphates must be completely dissolved in water, because the proportion of the dissolved phosphates significantly affects the pH value. The thus-prepared aqueous solutions are poured into an organic solvent such as ethanol, in the same manner as described above, respectively, and the precipitated fine particles are collected.

Preparation Procedure 2: Blending Electrolyte Composition

The above-obtained fine particles of inorganic salts, polyvinyl pyrrolidone, and an organic solvent were blended to form an electrolyte composition in the form of a paste. The followings are examples of the thus-blended compositions.

| Electrolyte Composition: Case 3 | |
| --- | --- |
| Mixture of fine particles of potassium chloride and phosphate | 0.25 g |
| Polyvinyl pyrrolidone | 1 g |
| Pentanol | 5 g |
| Electrolyte Composition: Case 4 (fine particles of buffering agent separately formed) | |
| Potassium chloride fine particle | 3.5 g |
| Phosphate fine particle | 0.5 g |
| Polyvinyl pyrrolidone | 1 g |
| Pentanol | 5 g |

The performance of the miniaturized oxygen electrode produced in Examples 1 and 2 was tested by measuring the dissolved oxygen concentration of a 10 mM buffered phosphoric acid solution having a pH value of 7.0 at an applied voltage of 0.6 V and a temperature of 25° C.

Figure 4:
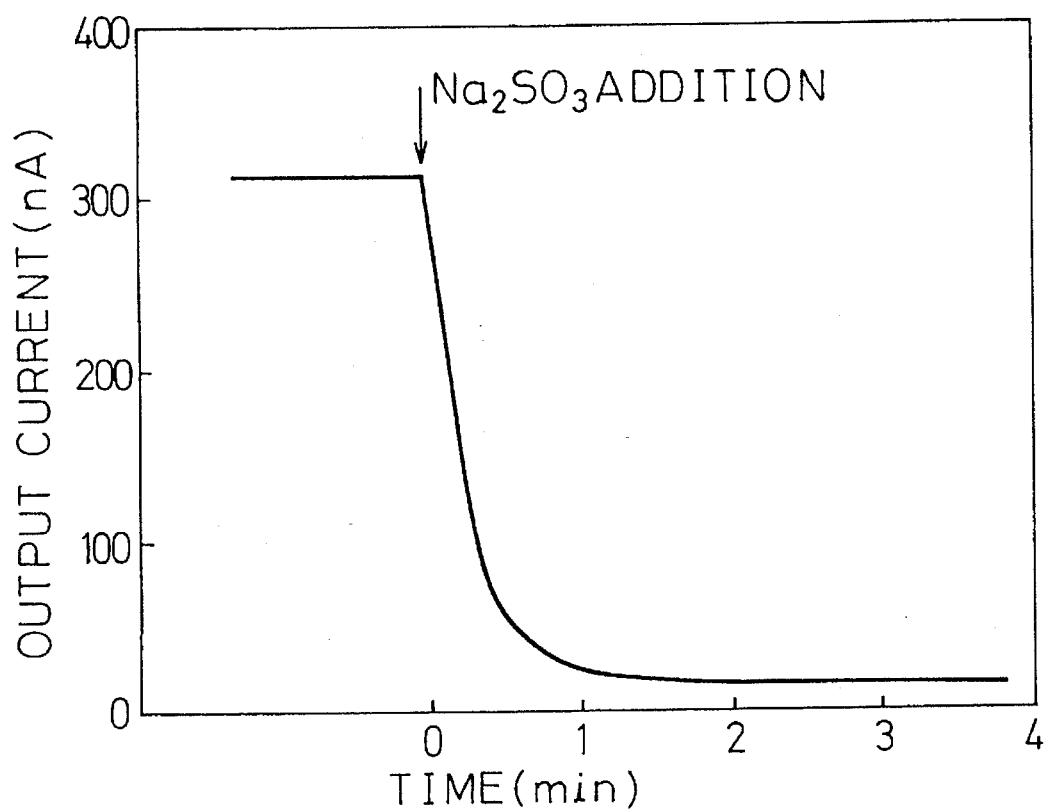
FIG. 4 is a graph showing a typical response of a miniaturized oxygen electrode according to the present invention, in terms of the relationship between the time elapsed from the addition of $Na_2SO_3$ and the output current.

FIG. 4 shows a response curve observed when sodium sulfite is added to a solution saturated with 100% oxygen, to instantaneously reduce the oxygen concentration to zero. The response time was 40 seconds, which corresponded to the variation of the dissolved oxygen concentration.

Figure 5:
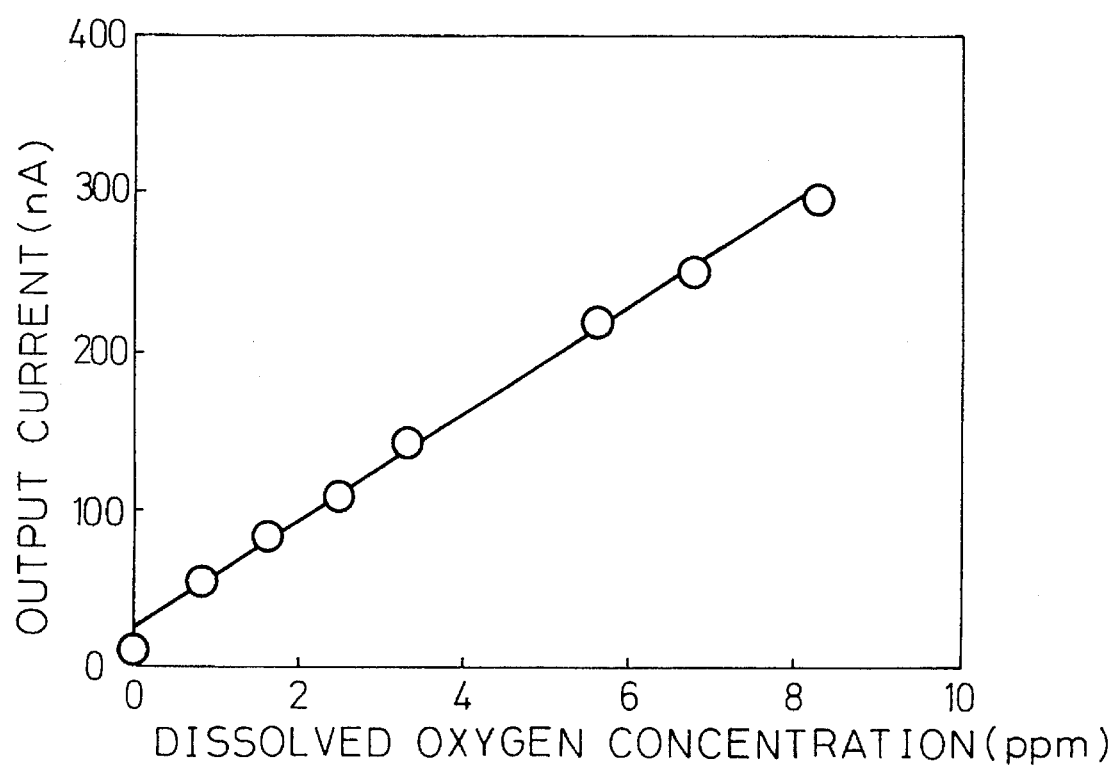
FIG. 5 is a graph showing the linear calibration curve of a miniaturized oxygen electrode according to the present invention, in terms of the relationship between the dissolved oxygen content and the output current.
Figure 6A:
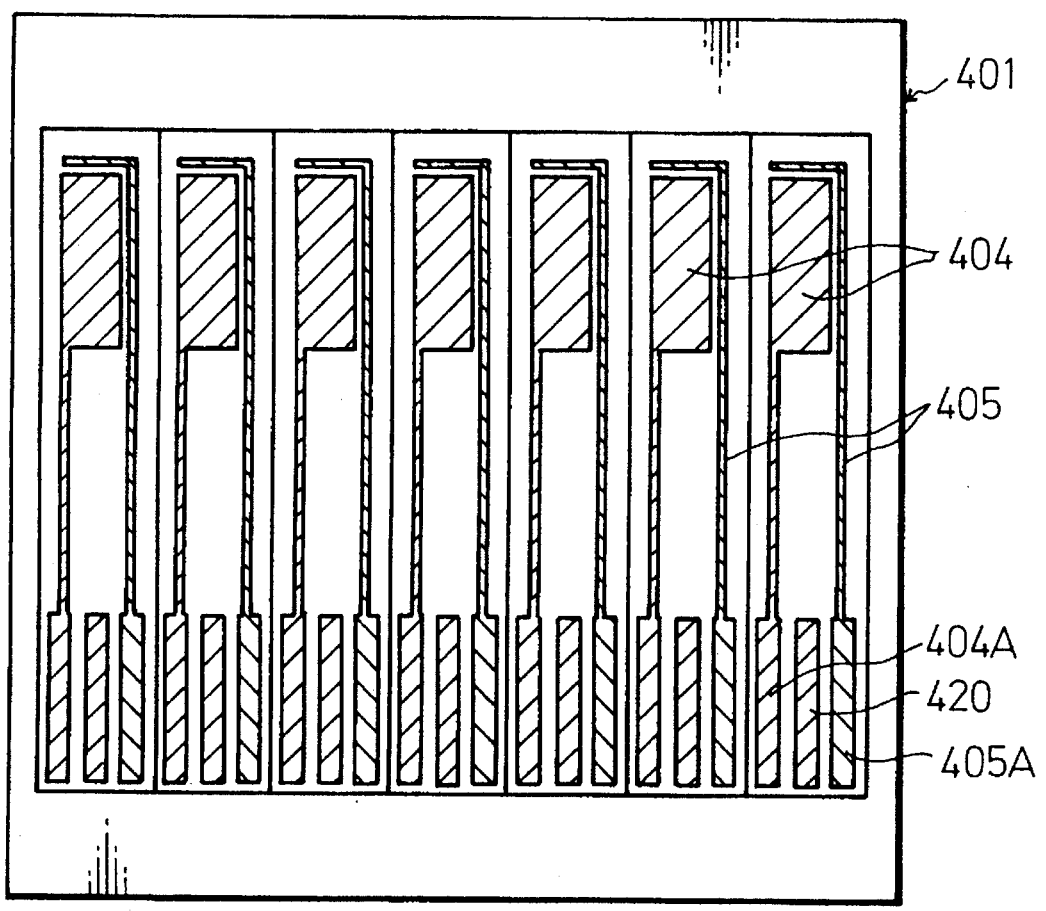
FIGS. 6(a) through (f) show a process sequence according to the present invention, in sectional and plan views.
Figure 6B:
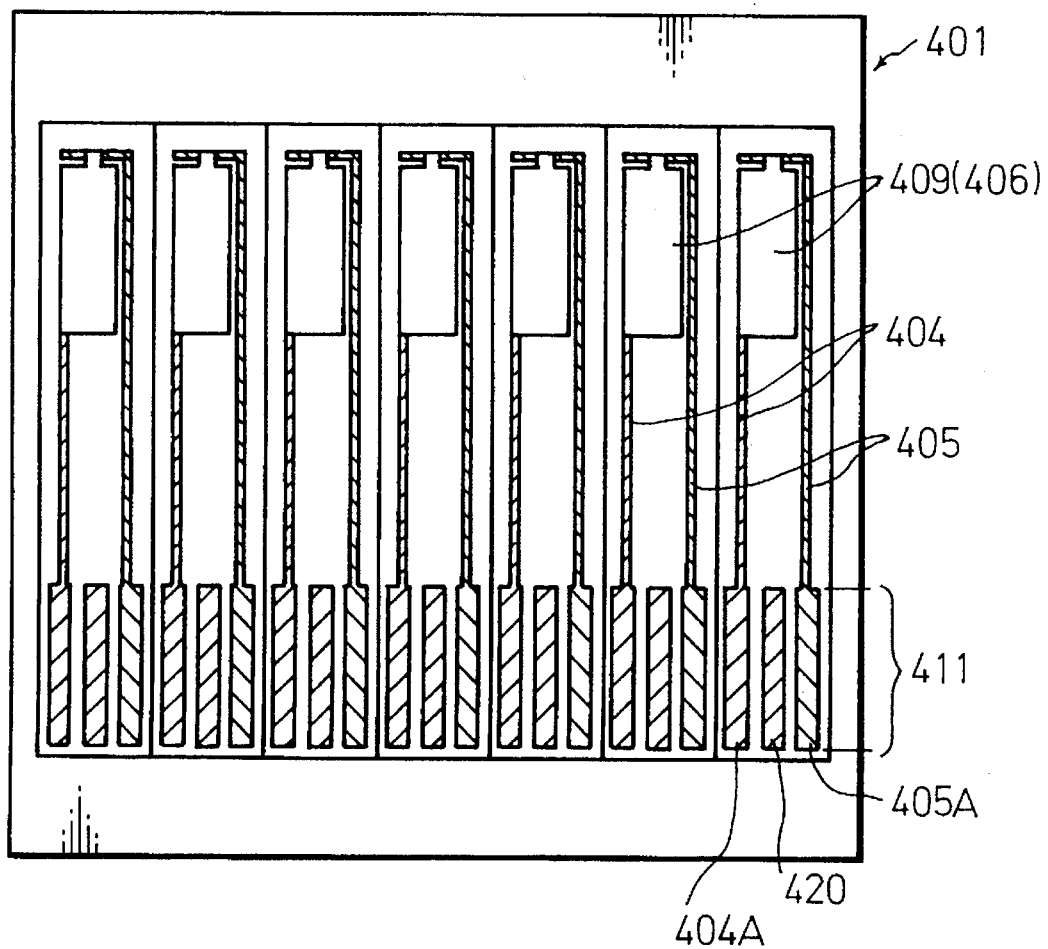
Figure 6C:
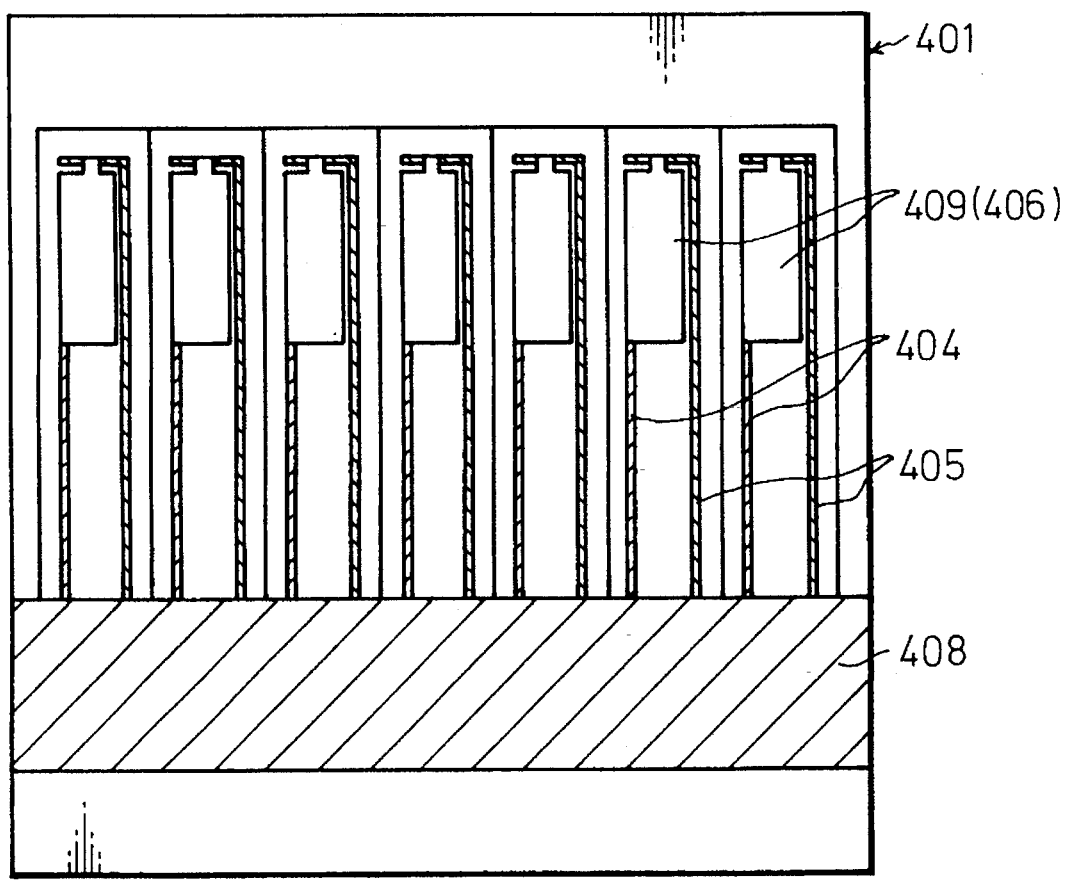
Figure 6D:
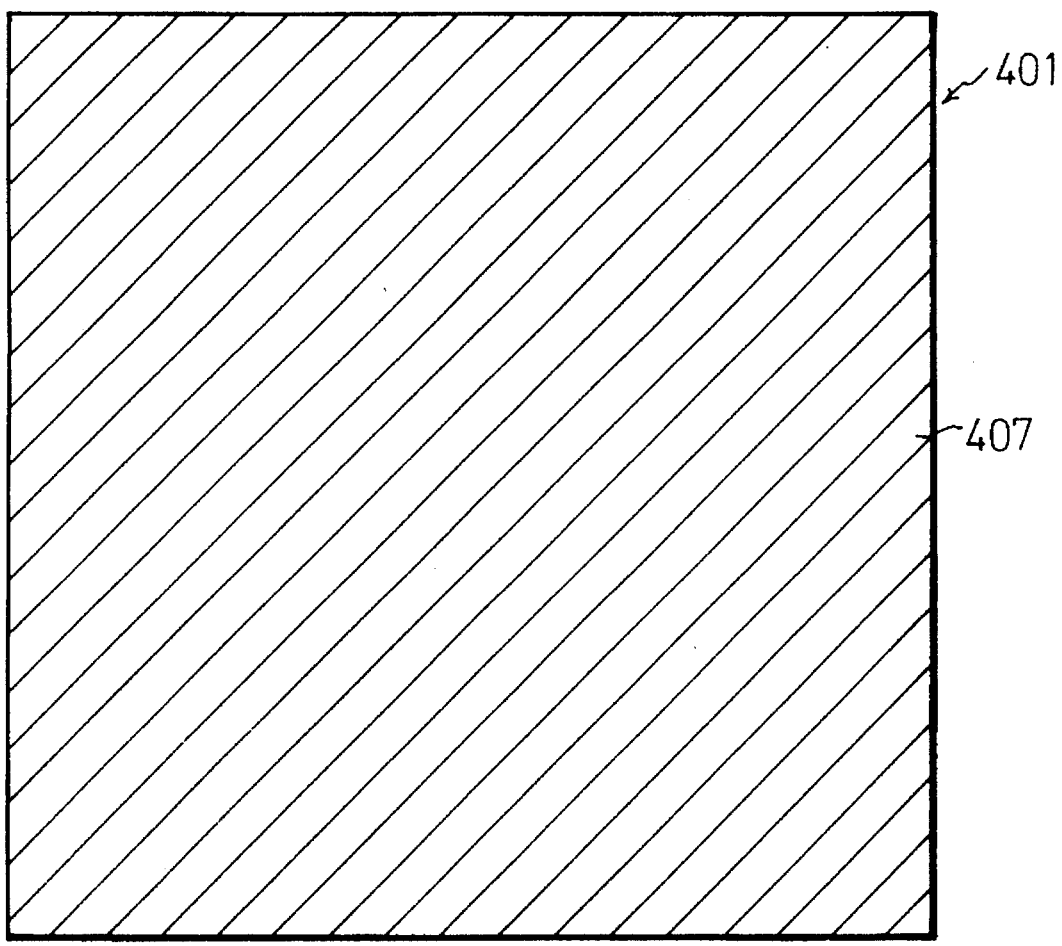
Figure 6E:
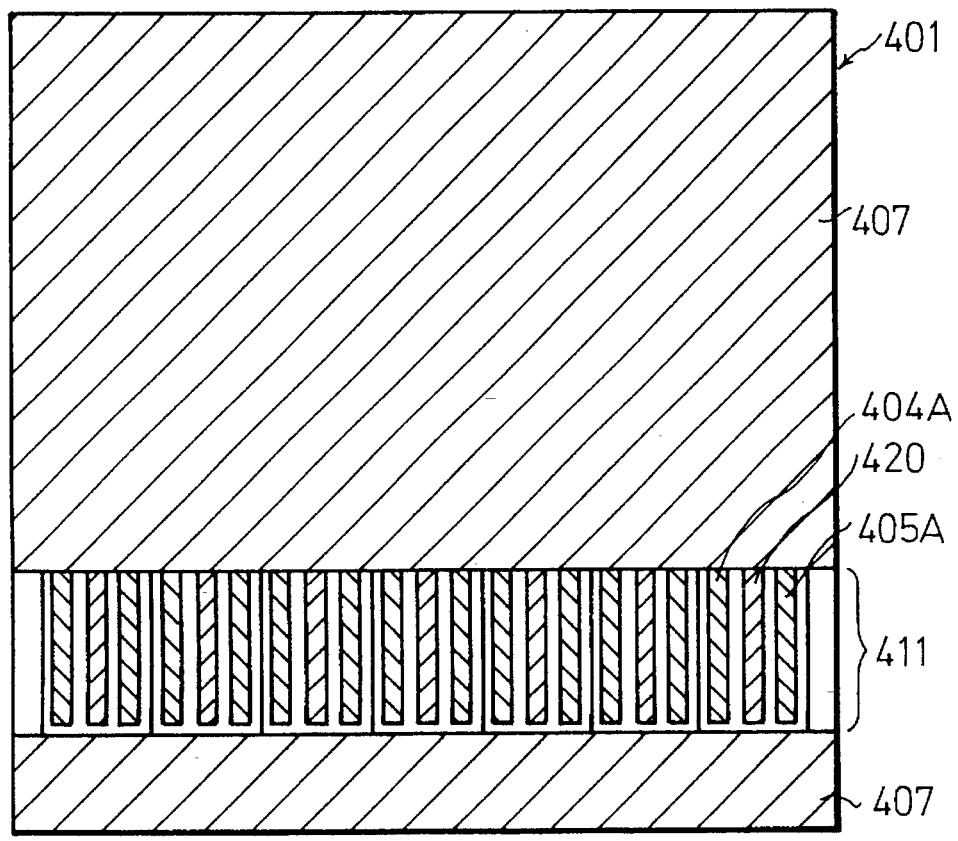
Figure 6F:
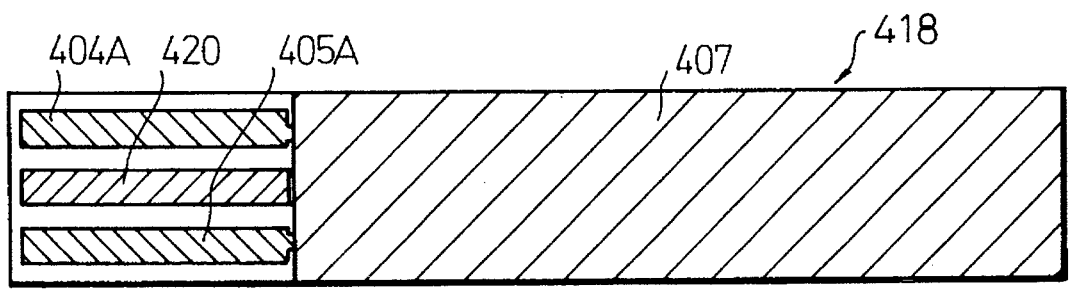
Figure 7A:
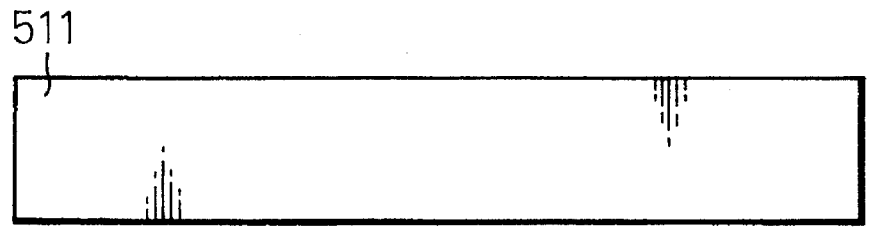
FIGS. 7(a) through (l) show a process sequence according to the present invention, in sectional and plan views.
Figure 7B:
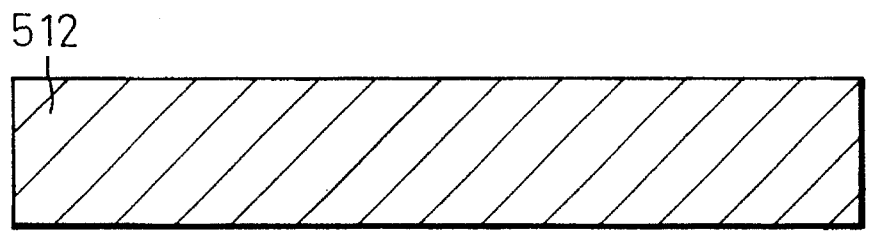
Figure 7C:
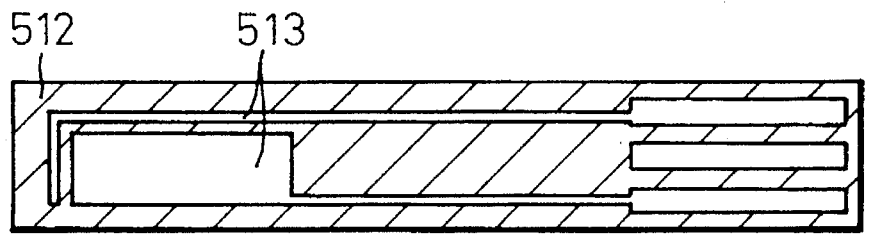
Figure 7D:
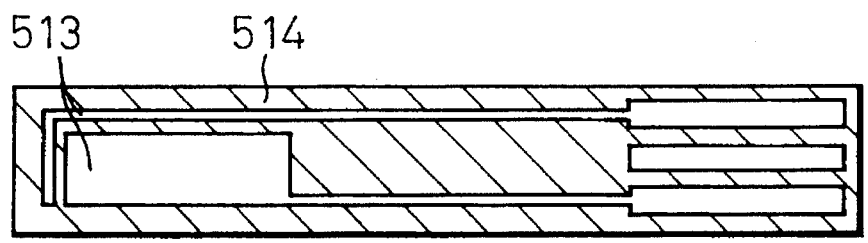
Figure 7E:
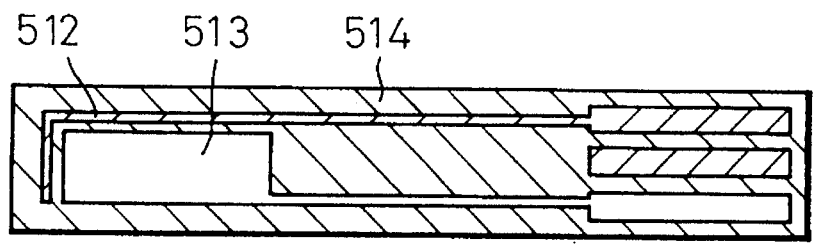
Figure 7F:
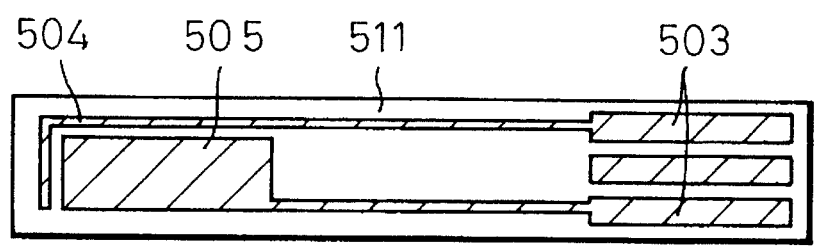
Figure 7G:
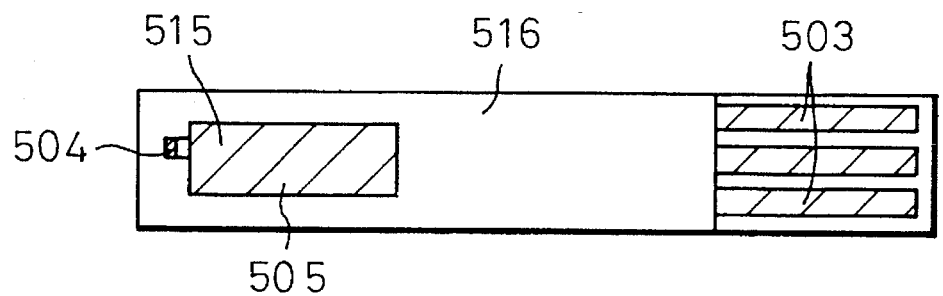
Figure 7H:
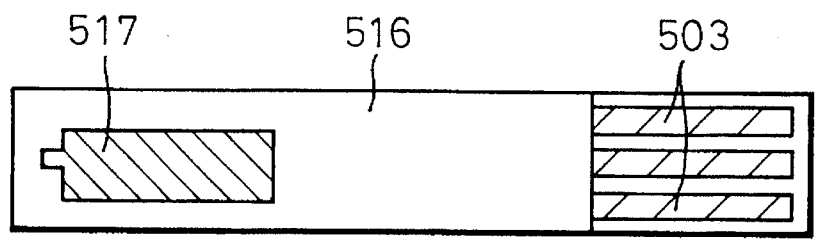
Figure 7I:
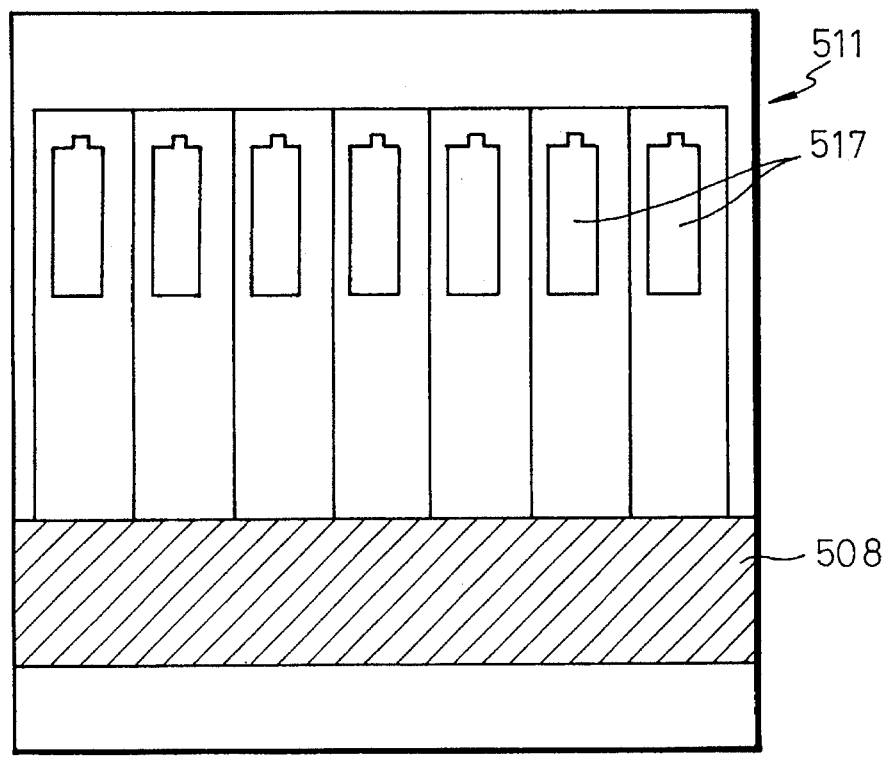
Figure 7J:
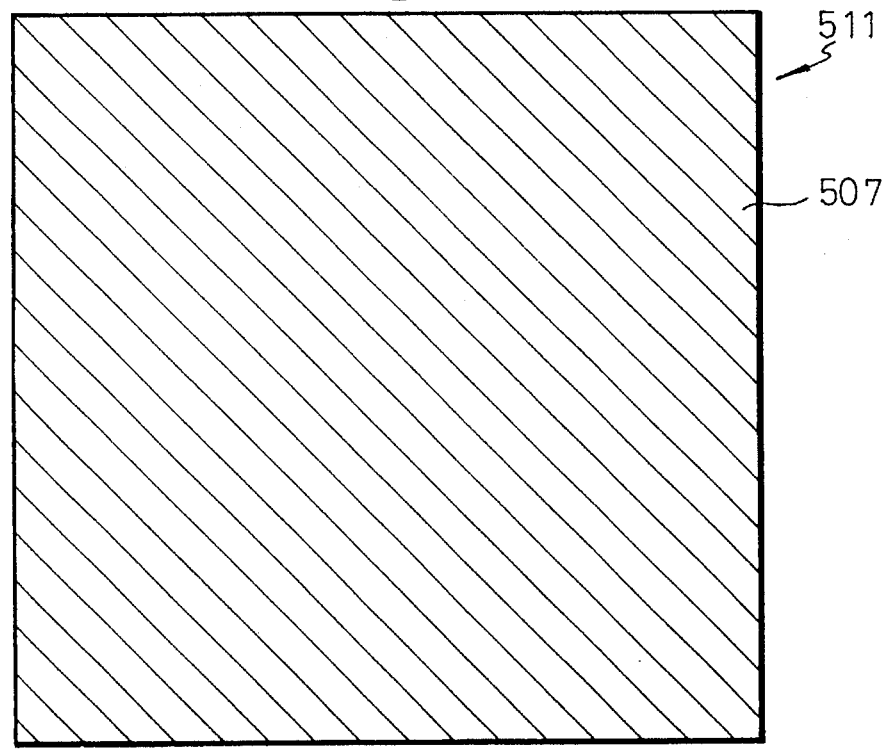
Figure 7K:
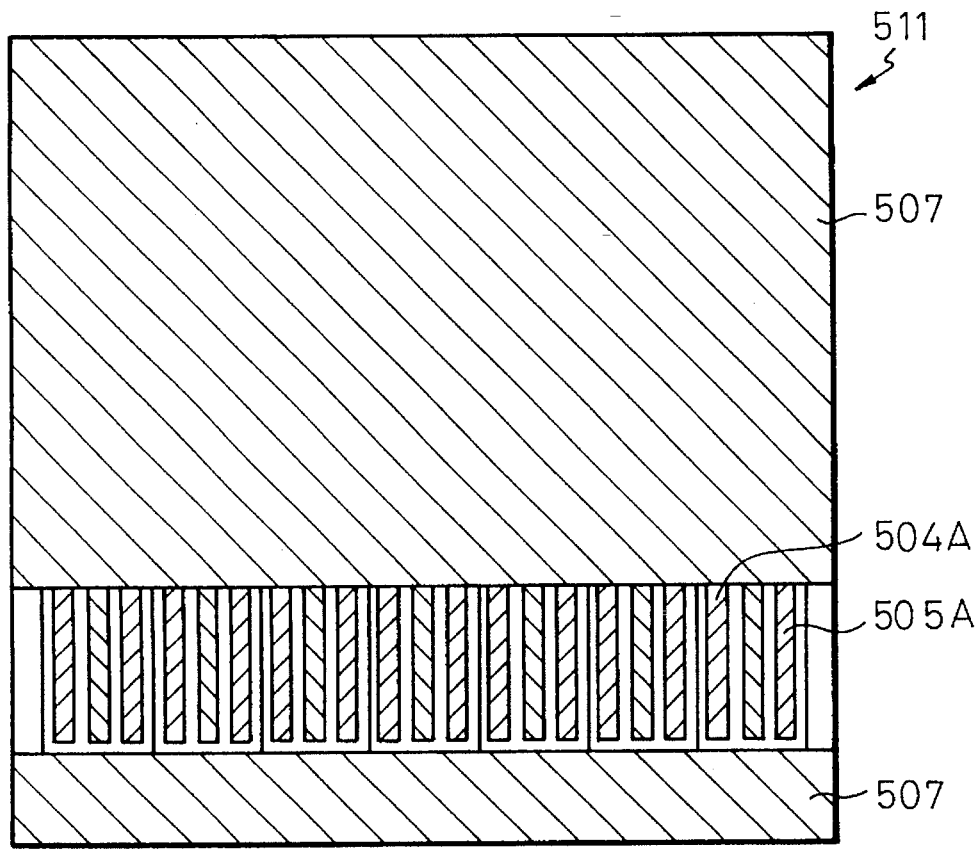
Figure 7L:
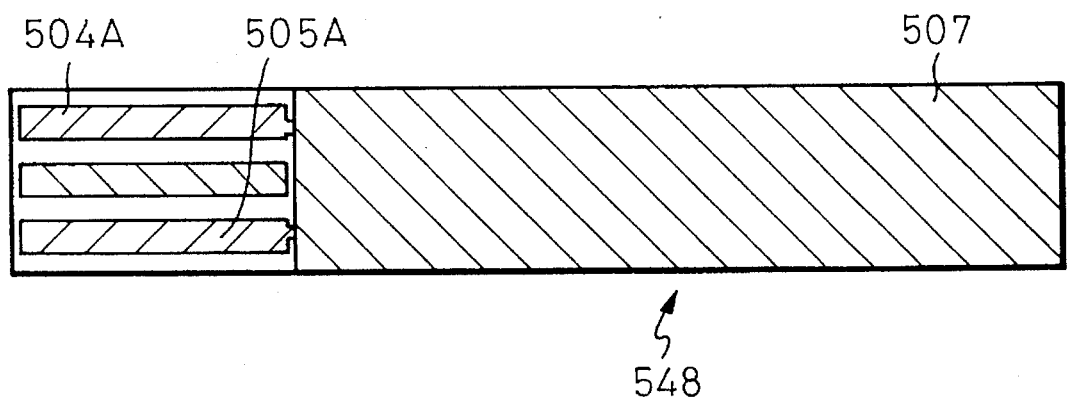

FIG. 5 shows a calibration curve obtained in this case, from which it is seen that a good linearity is ensured over the entire range of the dissolved oxygen concentration of from 0 ppm through 8 ppm, i.e., the saturation concentration.

Example 3

Referring to FIG. 6, a process sequence for producing a miniaturized oxygen electrode according to the present invention by using an electrically insulating flat substrate other than a silicon wafer will be described.

Step 1: Forming Component Electrode Pattern FIG. 6(a)

A 60 mm square, 1.6 mm thick, cleaned electrically insulating flat substrate 401 was prepared. The insulating substrate 401 may be made of glass, quartz, ceramics, plastics or other electrically insulating substances.

A component electrode pattern consisting of an anode 404 and a cathode 405 was formed on the insulating substrate 401 by either of the following procedures (a) and (b):

(a) A silver thin layer is formed by vacuum deposition and is etched to form a predetermined electrode pattern, in the same manner as used in preceding Examples 1 and 2.

(b) An electroconductive paste (Fujikura Kasei Co., D-1230 modified) is screen-printed on the substrate.

The component electrodes 404 and 405 have ends for external electrical connections or pads 404A and 405A, respectively.

An auxiliary pad 420 provided between the pads 404A and 405A can be used for a miniaturized oxygen electrode having a three-pole structure, for example.

Step 2: Screen-Printing Electrolyte Composition (FIG. 6(b))

The same electrolyte composition as used in Example 1 was screen-printed to fill a region 409 of the oxygen sensing site, and thereby form an electrolyte-containing material 406.

Step 3: Forming Pad Region Cover Film FIG. 6(c))

A thermosetting release coating (Fujikura Kasei Co., XB-801) was screen-printed at a pad region 411 containing the pads 404A and 405A and the auxiliary pad 420, to form a cover film 408 covering the pad region 411.

Step 4: Forming Oxygen Gas-Permeable Membrane (FIG. 6(d))

An oxygen gas-permeable membrane 407 having a double-layered structure was formed on the substrate 401 to entirely cover the upper surface of the substrate 401. The lower and the upper layers of the membrane 407 were formed by applying a negative-type photoresist (Tokyo Ohka Kogyo Co., Ltd., OMR-83, viscosity 100 cP) and a silicone resin (Toray-Dow Corning Silicone Co., SE9176) by spin coating, respectively, and then curing the applied layers.

Step 5: Exposing Pad Region (FIG. 6(e))

The cover film 408 formed on the pad region 411 was peeled with a pincette to selectively remove the oxygen gas-permeable membrane 407 in that portion, and thereby expose the pads 404A and 405A of a miniaturized oxygen electrode. The auxiliary pad 420 was simultaneously exposed.

Step 6: Separating Miniaturized Oxygen Electrodes (FIG. 6(f))

A plurality of miniaturized oxygen electrodes were collectively formed on the electrically insulating substrate 401 at one time by the preceding Steps 1 to 6, and were cut into chips by a dicing saw. The shown example provided seven chips of miniaturized oxygen electrodes 418 from a single substrate, simultaneously.

Although the preceding Examples formed the component electrodes of silver, the component electrodes may be formed of gold instead of silver, or a cathode and an anode may be formed of gold and silver, respectively.

For example, the component electrodes can be formed of gold instead of silver by a partial modification of the process steps of Example 1, as follows.

Example 4

Steps 8 and 10 of Example 1 were modified in the following manner.

In Step 8 (FIGS. 3($g1$) and 3($g2$)), the same operation was performed as in Example 1, except that a gold thin layer 315 (4000 Å thick) was vacuum deposited instead of the silver thin layer 315 (4000 Å thick).

The subsequent Step 9 (FIGS. 3($h1$) and 3($h2$)) was performed in the same manner as in Example 1.

In Step 10 (FIGS. 3($i1$) and 3($i2$)), the same operation was performed as that in Example 1, except that the wafer 301 was immersed in an etchant for gold (KI/4 g+$I_2$/1 g+water/ 40 ml) instead of the etchant for silver.

These modifications provided a miniaturized oxygen electrode having a component electrode formed of gold.

A miniaturized oxygen electrode having a gold cathode and a silver anode may be produced in the following manner.

Example 5

Referring to FIG. 7, a process sequence for producing a miniaturized oxygen electrode having a gold cathode and a silver anode according to the present invention by using a glass substrate will be described.

Step 1: Cleaning Substrate (FIG. 7(a))

A 60 mm square, 1.6 mm thick glass substrate 511 was thoroughly washed with a detergent (for example, Furuuchi Kagaku Co., Semico Clean 56) and acetone.

Step 2: Forming Thin Layers of Chromium, Gold and Silver (FIG. 7(b))

A chromium thin layer (400 Å thick, for example), a gold thin layer (4000 Å, for example) and a silver thin layer 512 (4000 Å thick, for example) were formed on the substrate 511, in that order, by a vacuum deposition. The chromium thin layer ensures a good adhesion between the glass substrate 511 and component electrodes of gold and silver.

Step 3: Forming Photoresist Pattern (FIG. 7(c))

A positive-type photoresist (for example, Tokyo Ohka Kogyo Co., Ltd., OFPR-800, 20 cP or OFPR-5000, 50 cP) was applied on the silver thin layer 512 and prebaked at 80° C. for 30 min. The thus-formed photoresist layer was exposed to light and developed to form a photoresist pattern 513 corresponding to all component electrodes.

Step 4: Etching Gold and Silver Thin Layers (FIG. 7(d))

The substrate 511 was immersed in an etchant for silver (for example, 29% $NH_4OH$/1 ml+31% $H_2O_2$/1 ml+water/20 ml) to pattern the silver thin layer 512. The substrate 511 was then immersed in an etchant for gold (for example, KI/4 g+$I_2$/1 g+water/40 ml) to pattern the gold thin layer.

This exposed the chromium thin layer 514 in the portion not covered with the photoresist layer.

Step 5: Re-Patterning Photoresist Pattern (FIG. 7(e))

The positive-type photoresist layer 513 was exposed to light and developed again so that the photoresist pattern 513 remained only in the portion at which an anode is to be formed, and the other portion of the photoresist pattern 513 was removed to expose the silver thin layer 512.

Step 6: Patterning Component Electrodes (FIG. 7(f))

The substrate 511 was immersed in an etchant for silver to remove the silver thin layer exposed in the preceding Step 5, and thereby expose the underlying gold thin layer, with the result that the gold cathode 504, including part of the extended card edge portion (or pad) 503, and part of a floating card edge portion (or pad), were exposed. The substrate was then immersed in an etchant for chromium (for example, NaOH/0.5 g+$K_3$ Fe$(CN)_6$/1 g+water/4 ml) to remove an open portion of the chromium thin layer 514. The substrate was immersed in acetone to entirely remove the photoresist pattern 513, and thereby expose the silver anode 505 including part of the extended card edge portion (or pad) 503.

This completed the formation of the entire arrangement of component electrodes including the gold cathode 504 and the silver anode 505.

Step 7: Forming Photoresist Pattern (FIG. 7(g))

A negative-type photoresist (for example, Tokyo Ohka Kogyo Co., Ltd., OMR-83, 60 cP) was applied to the entire upper surface of the substrate 511 by spin coating and prebaked at 70°–80° C. for 30 min. After an exposure to light and development, the photoresist was postbaked at 150° C. for 30 min. to form a photoresist pattern 516, which covered the substrate surface except for an oxygen sensing site of the silver anode 505, part of the gold cathode 504, and the card edge portion (or pad) 503.

Step 8: Screen-Printing Electrolyte Composition (FIG. 7(h))

An electrolyte composition of the present invention was screen-printed on the oxygen sensing site 515 defined by the photoresist pattern 516, to form an electrolyte-containing material 517.

Step 9: Forming Pad Region Cover Film (FIG. 7(i))

A thermosetting release coating (Fujikura Kasei Co., XB-801) was screen-printed on the pad region (or card edge portion) 503 at a thickness of 100 μm, and then cured by heating at 150° C. for 10 min. to form a cover film 508.

Step 10: Forming Oxygen Gas-Permeable Membrane (FIG. 7(j))

A oxygen gas-permeable membrane 507 having a double-layered structure was formed on the glass substrate 511 to entirely cover the substrate upper surface. The lower layer of the membrane 507 was first formed by spin-coating a negative-type photoresist (Tokyo Ohka Kogyo Co., Ltd., OMR-83, viscosity 100 cP), prebaking at 80° C. for 30 min., exposing the entire substrate surface to light, and postbaking at 150° C. for 30 min. The upper layer was then formed by spin-coating a silicone resin (Toray-Dow Corning Silicone Co., SE9176) and curing by heating at 70° C. for 30 min. in an oven moistened with the water contained in a Petri dish or a beaker placed in the oven.

Step 11: Exposing Pads (FIG. 7(k))

The cover film 508 formed in the pad region 503 was peeled off with a pincette to selectively remove the oxygen gas-permeable membrane 507 in that portion, and thereby expose the pads (or card edges) 504A and 505A of a miniaturized oxygen electrode.

The selective removal of the oxygen gas-permeable membrane 507 was effected in such a way that, when the cover film 508 was peeled off, the oxygen gas-permeable membrane 507 was cut by the edge of the cover film 508 between the membrane portion positioned on the cover film 508 and the other membrane portion away from the cover film 508.

The portion of oxygen gas-permeable membrane remaining on the glass substrate strongly adhered to the substrate and was not exfoliated by the later treatments, including a water vapor treatment describe later. The oxygen gas-permeable membrane also ensures a high reliability such that it does not fracture when attached to a catheter and used in a medical care, or when used for monitoring the oxygen concentration in a fermenter subjected to a sterilization at a temperature of 120° C. and a differential pressure of 1.2 atm. for about 15 min.

Step 12: Separating Miniaturized Oxygen Electrodes (FIG. 7(l))

A plurality of miniaturized oxygen electrodes were collectively formed on the glass substrate 511 at one time and were cut into chips by a dicing saw. The shown example provides seven miniaturized oxygen electrodes from a single substrate at one time.

The oxygen gas-permeable membrane strongly adhered to the substrate and did not exfoliate during a cutting thereof along a scribe line, and further, did not exhibit a lowered reliability when subjected to a reliability test.

The miniaturized oxygen electrode according to the present invention can be applied to any clark type device for electrochemically detecting oxygen, including Galvani type, and three-pole type oxygen electrodes.

FIGS. 8(a), (b) and (c) show an example of the three-pole type miniaturized oxygen electrode, wherein FIG. 8(b) shows an unfinished structure in which an oxygen gas-permeable membrane is not yet formed.

Figure 8C:
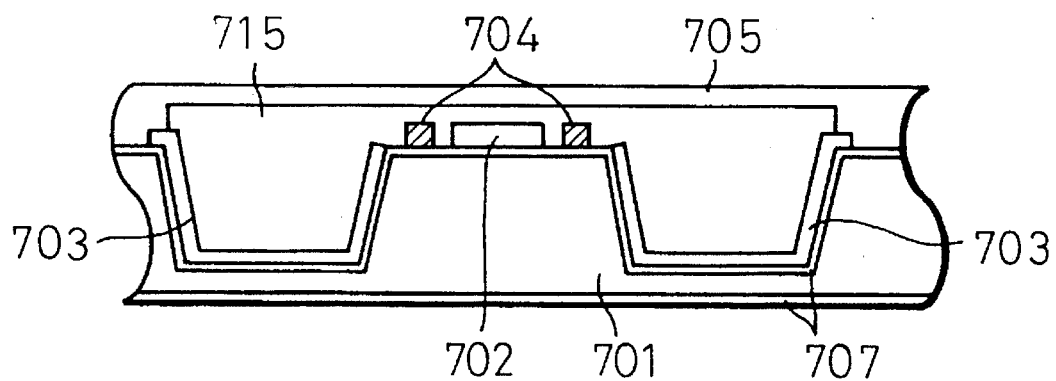

A working electrode 702, a counter electrode 703 and a reference electrode 704 are formed on a silicon wafer 701 (see FIG. 8(b)) and an oxygen gas-permeable membrane 705 covers the surface except for pads 702A, 703A and 704A of the respective electrodes. FIG. 8(c) shows an I—I section of an oxygen sensing site, in which an electrolyte composition 715 is filled in grooves formed in the silicon wafer to form a electrolyte-containing material.

Example 6

A three-pole type miniaturized oxygen electrode according to the present invention and having a basic structure as shown in FIGS. 8(a) to (c) was produced according to the present invention in the following sequence.

Figure 9:
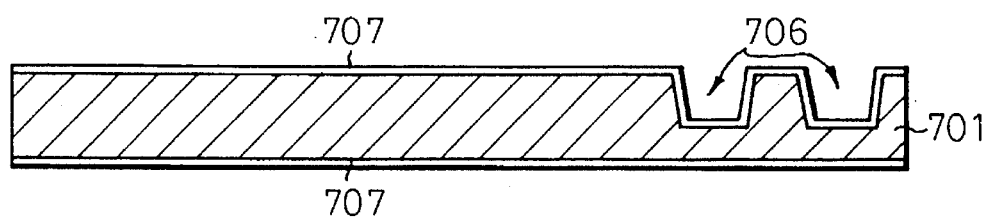
FIGS. 9(a) through (e) show a process sequence for producing a three-pole miniaturized oxygen electrode, according to the present invention, in sectional and plan views.
Figure 9:
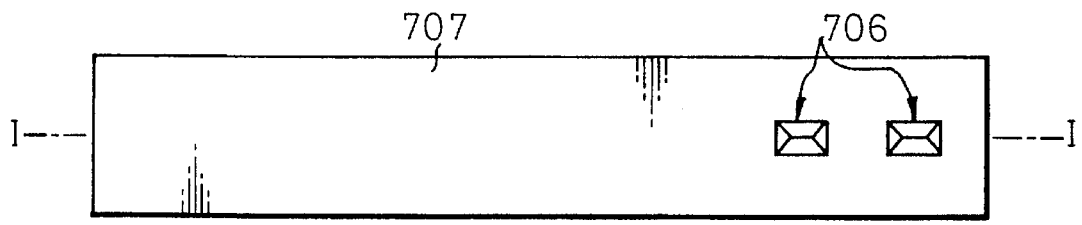
Figure 9:
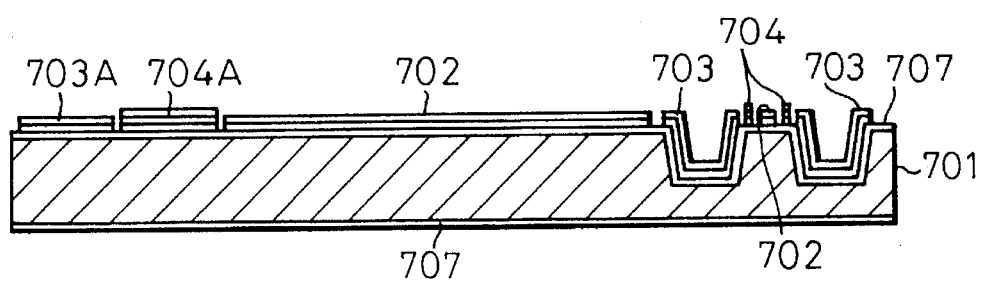
Figure 9:
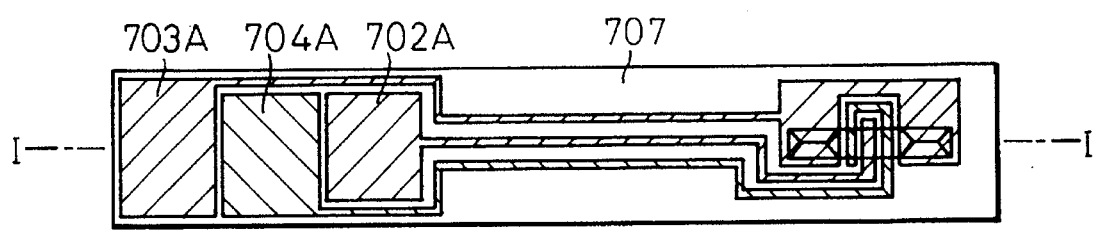
Figure 9:
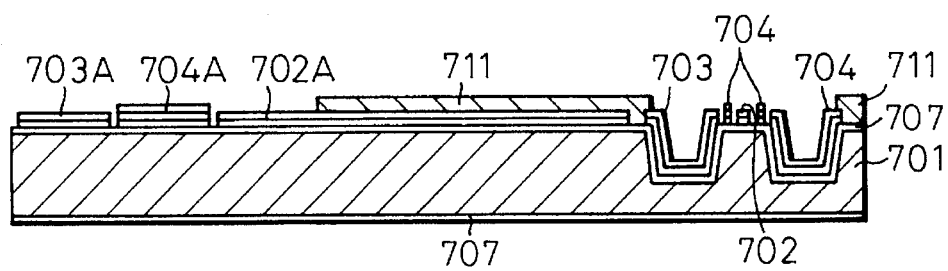
Figure 9:
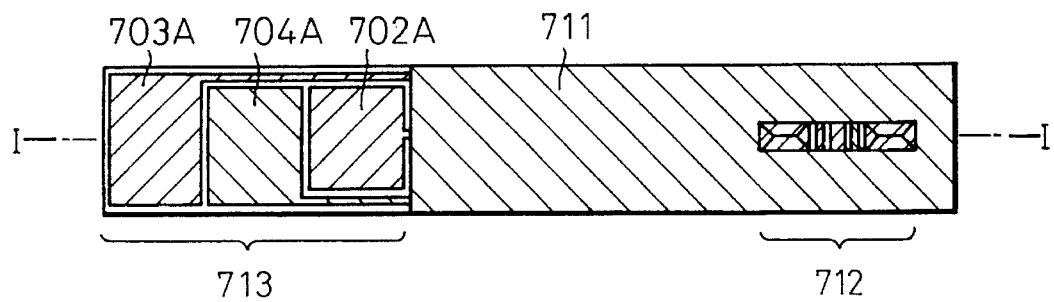
Figure 9:
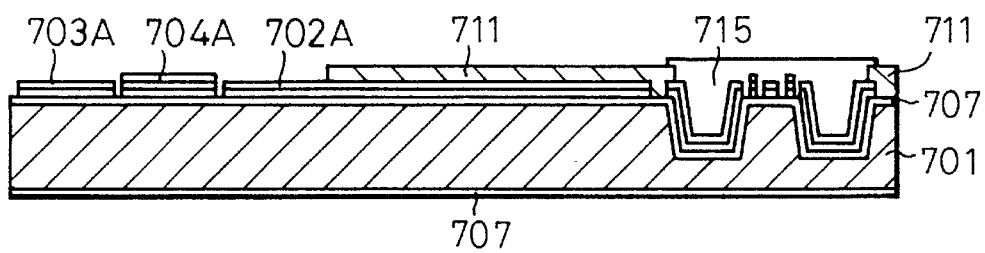
Figure 9:
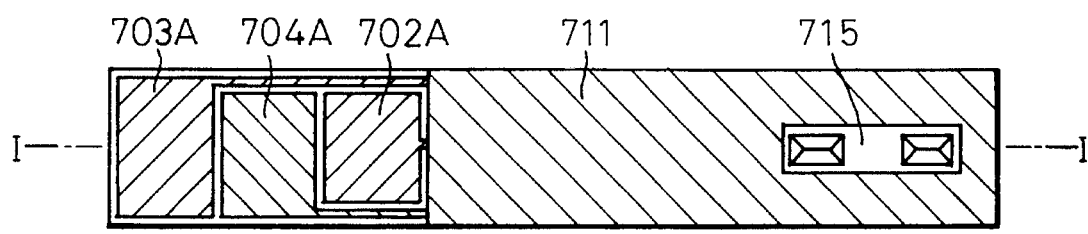
Figure 9:
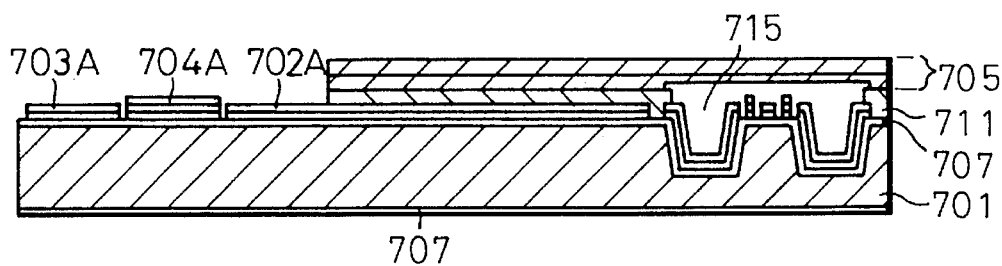
Figure 9:
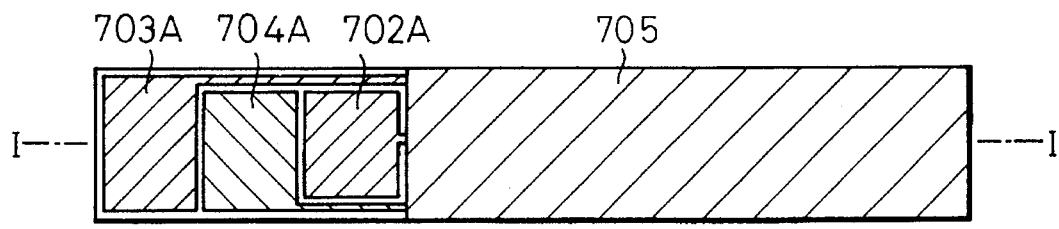

Step 1: Forming Grooves for Receiving Electrolyte-Containing Material (FIG. 9(a1) and 9(a2))

In the same sequence as carried out in Steps 1 through 7 of Example 1, grooves 706 for receiving an electrolyte-containing material and an SiO₂ insulating layer 707 were formed on both sides of a silicon wafer 701.

Step 2: Forming Component Electrode Pattern
(FIGS. 9(*b*1) and 9(*b*2))

In the same sequence as carried out in Steps 2 through 6 of Example 5, a working electrode 702 and a counter electrode 703, both of gold, and a reference electrode 704 of silver were formed.

Step 3: Forming Photoresist Pattern FIGS. 9(*c*1) and 9(*c*2))

By the same operation as carried out in Step 11 of Example 1, a photoresist pattern 711 was formed to cover the substrate surface except for a region 712 of the oxygen sensing site and a pad region 713.

Step 4: Screen-Printing Electrolyte Composition
(FIGS. 9(*d*1) and 9(*d*2))

By the same operation carried out in Step 12 of Example 1, an electrolyte composition 715 was screen-printed on the oxygen sensing site 712.

Step 5: Forming Pad Region Cover Film (not shown)

By the same operation as carried out in Step 13 of Example 1, a removable cover film was formed.

Step 6: Forming Oxygen Gas-Permeable Membrane (not shown)

By the same operation as carried out in Step 14 of Example 1, an oxygen gas-permeable membrane was formed.

Step 7: Exposing Pads (FIGS. 9(*e*1) and 9(*e*2))

By the same operation as carried out in Step 15 of Example 1, pads 702A, 703A and 704A were exposed.

Step 8: Separating Miniaturized Oxygen Electrodes (not shown)

By the same operation as carried out in Step 16 of Example 1, a number of miniaturized oxygen electrode formed on the silicon wafer were cut into chips.

In Examples 1 through 6, miniaturized oxygen electrodes were produced at a yield of 98% or more and exhibited a good response characteristic, i.e., an output fluctuation of less than ±3% when measured in water saturated with oxygen.

The produced miniaturized oxygen electrode is preserved in the dried condition and can be made operative when supplied with water through the oxygen gas-permeable membrane by water vapor sterilization (for example, at 121° C. and 2.2 atm.), immersion in water, exposure to a saturated water vapor, etc.

Figure 10:
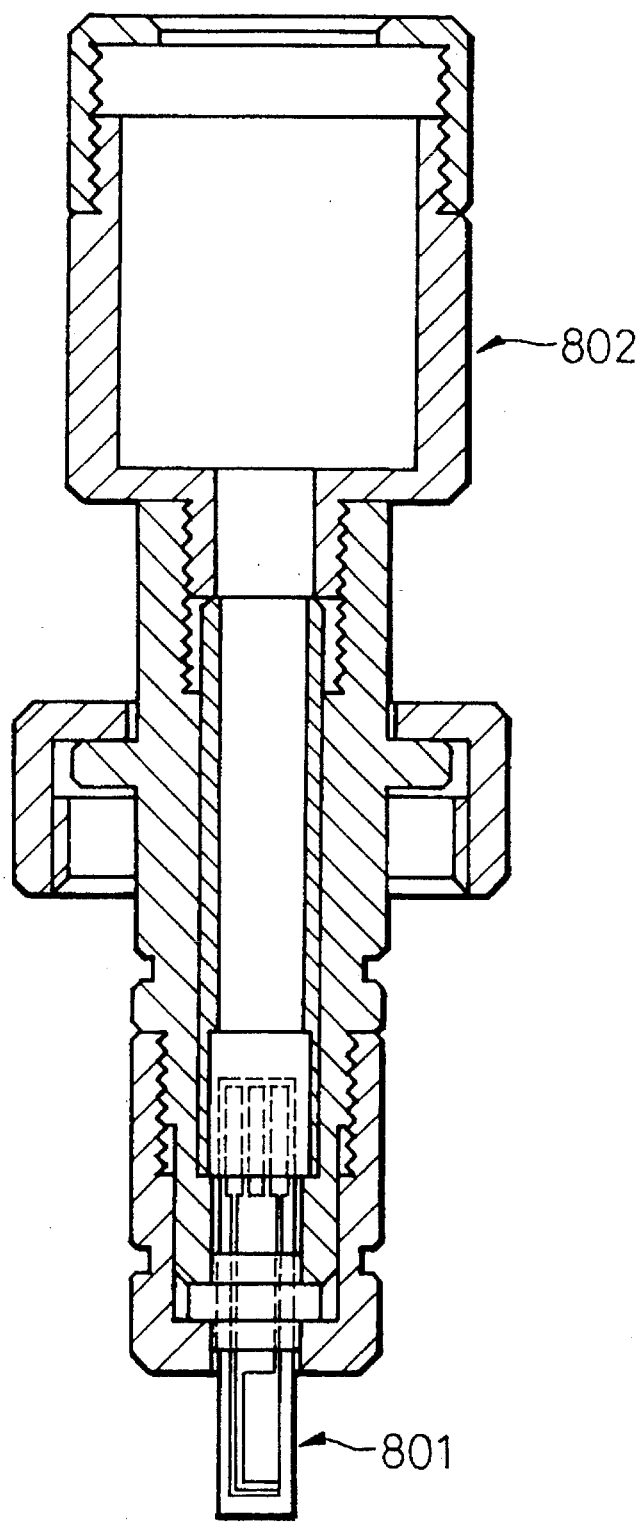
FIG. 10 shows a miniaturized oxygen electrode mounted on an adapter for use in a fermenter, in sectional view.

When an miniaturized oxygen electrode is used for a fermenter, the above-mentioned preparation or water supply may be conveniently effected together with sterilization of the culture medium. As shown in FIG. 10, a miniaturized oxygen electrode 801 of the present invention is conveniently attached to a special adaptor 802 designed for a fermenter (proposed by the present inventors and others in Japanese Patent Application No. 1-231,708).

The external electrical connection of a miniaturized oxygen electrode is usually carried out by inserting the card edge portion (or pad portion) 503 to a card edge connecter (for example, Fujitsu Ltd., Type 760).

Figure 11:
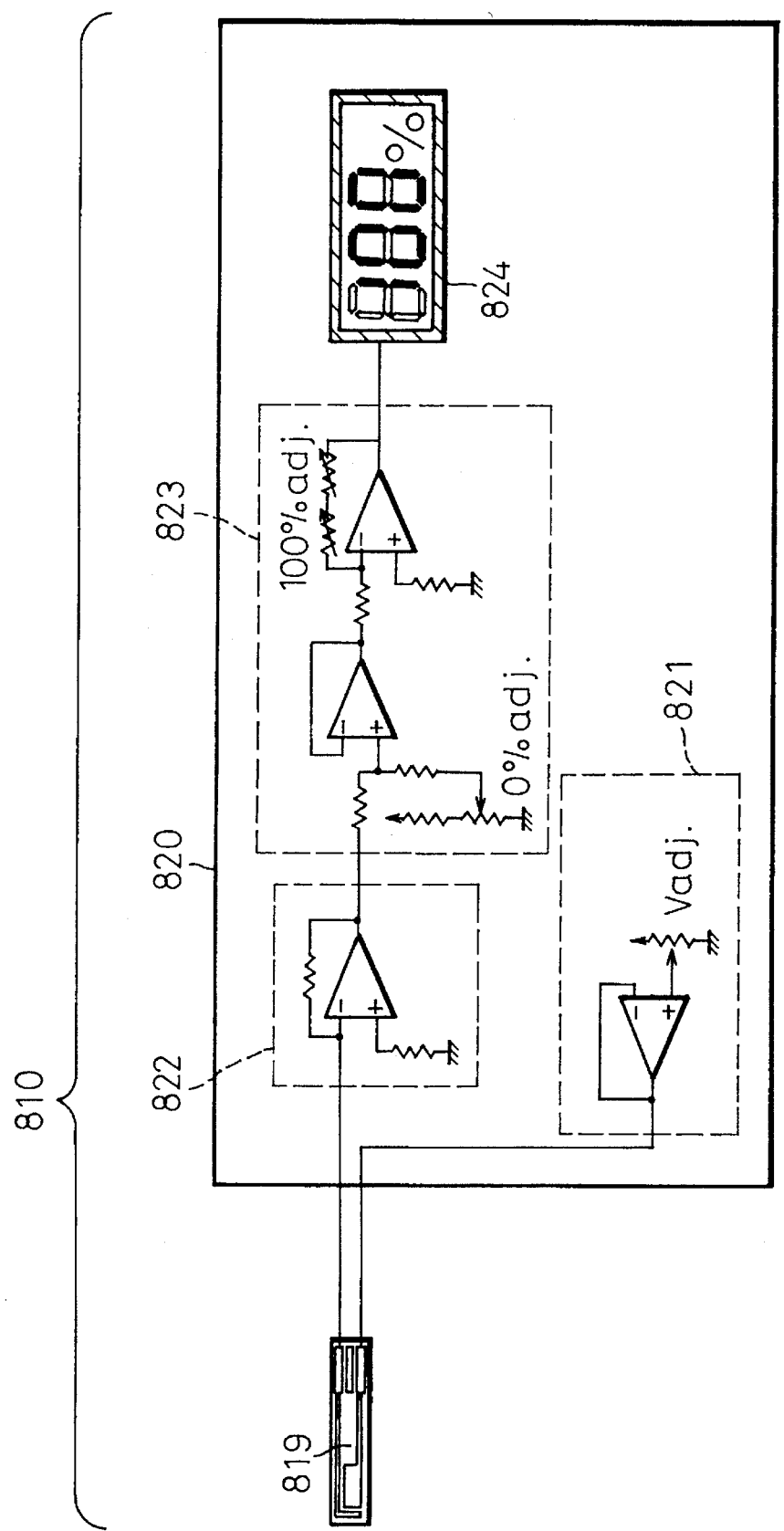
FIG. 11 shows an arrangement of a device for measuring the oxygen concentration in which a miniaturized oxygen electrode according to the present invention is applied.

FIG. 11 shows an arrangement of an oxygen concentration measuring device in which a miniaturized oxygen electrode of the present invention is used. An oxygen concentration measuring device 810 is composed of a miniaturized oxygen electrode 819 of the present invention and a controller 820. The controller 820 is composed of a voltage supply unit 821 for generating a voltage to be supplied to the oxygen electrode 819, a current-to-voltage converter unit 822 for converting an output current from the oxygen electrode 819 to a voltage, a calibration unit 823 for calibrating an output voltage from the converter unit 822 at the oxygen concentrations of 0% and 100%, and a display unit 824. The device 810 measures the dissolved oxygen concentration in many kinds of solutions and the oxygen concentration of gas phases.

As herein described, the present invention provides a miniaturized oxygen electrode which can be mass-produced at a high efficiency by collectively and uniformly processing a substrate as a whole by using the semiconductor process, a production process thereof, and an electrolyte composition able to be advantageously used therefor.

According to the present invention, there is also provided a further improved miniaturized oxygen electrode to solve an aforementioned problem in that it does not provide sufficient stability when continuously operated for a long time, as specifically described in the following examples.

Example 7

Figure 12A:
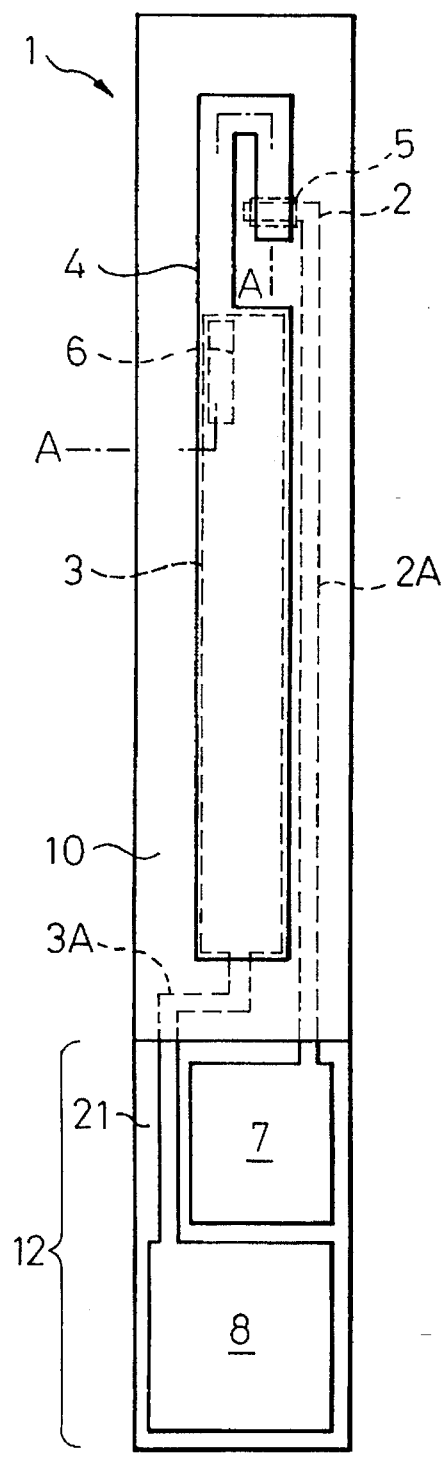
FIGS. 12(A) and 12(B) are plan views showing (A) one chip of a miniaturized oxygen electrode and (B) a number of miniaturized oxygen electrode formed on a single silicon wafer, respectively.
Figure 13A:
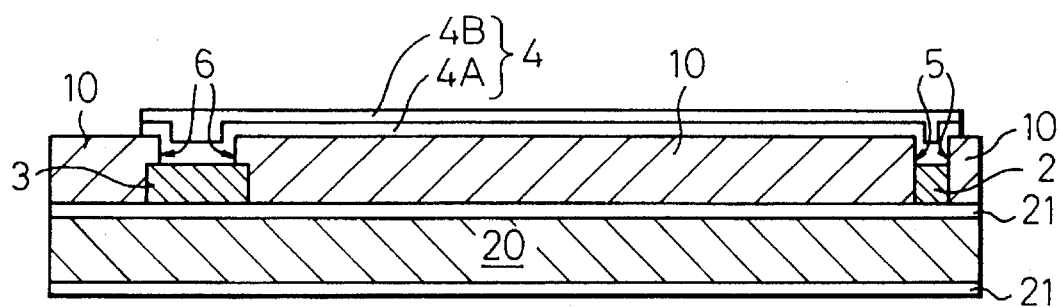
FIGS. 13(A) and 13(B) are cross sectional views of miniaturized oxygen electrodes according to the present invention, in which electrolyte-containing materials have (A) double-layered and (B) single-layered structures, respectively.
Figure 13B:
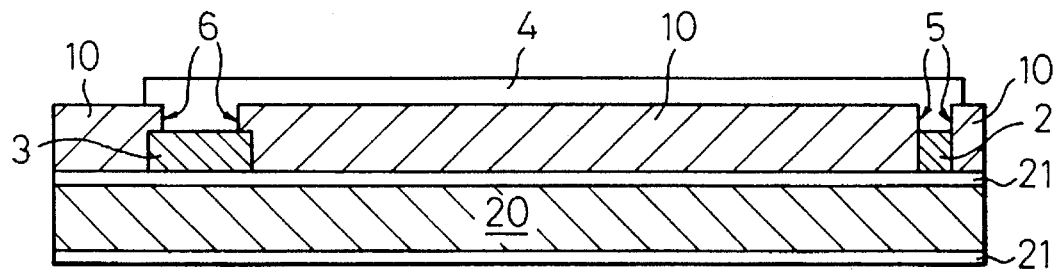

FIGS. 13(A) and 13(B) show a further improved miniaturized oxygen electrode having (A) a double-layered electrolyte-containing material 4 and (B) a miniaturized oxygen electrode having a single-layered electrolyte-containing material 4, respectively, in cross sectional views along line A—A of FIG. 12(A).

In the further improved miniaturized oxygen electrode of the present invention shown in FIG. 13(A), an electrolyte-containing material 4 connecting a cathode 2 and an anode 3 is composed of two layers, i.e., a first layer 4A and a second layer 4B. The first layer 4A contains no electrolytes but is connected to the cathode 2 whereas the second layer 4B contains an electrolyte and is not connected to the cathode 2. The first layer 4A and the second layer 4B are connected to each other. In this example, the first layer 4A is connected at one end to the cathode and at the other end to the anode 3, respectively, whereas the second layer 4B is laminated onto the first layer 4A over the entire length of the first layer 4A.

FIGS. 14(A) through 14(D) show different arrangements of a first layer 4A (not containing electrolytes) and a second layer 4B (containing an electrolyte) of an electrolyte-containing material 4, in cross sectional views along line A—A of FIG. 12(A).

Figure 14A:
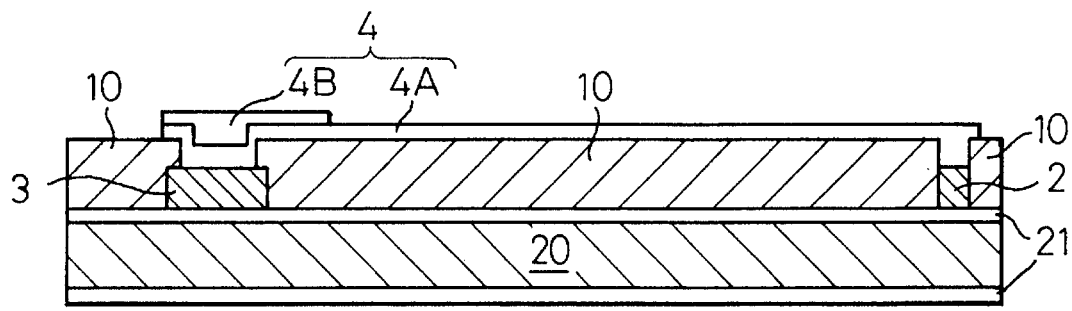
FIGS. 14(A), 14(B), 14(C), and 14(D) are cross sectional views showing various embodiments of double-layered electrolyte-containing materials according to the present invention.

In the arrangement shown in FIG. 14(A), a first layer 4A not containing electrolytes is connected to the cathode 2 and the anode 3 on both ends, respectively, whereas a second layer 4B containing an electrolyte is overlaid on the first layer 4A only in and near the region of connection to the anode 3. When the electrolyte concentration is relatively low, the arrangement shown in FIG. 13(A), in which the second layer 4B is overlaid on the first layer 4A over the entire length of the latter, satisfactorily prevents the electrolyte-caused cathode deterioration from occurring during water introduction using boiling water or high temperature water vapor. However, with an increased electrolyte concentration, the arrangement shown in FIG. 13(A) fails to prevent the cathode deterioration. In such a case, the second layer 4B is provided only in and near the region of connection to the anode 3 as shown in FIG. 14(A), so that there is no electrolyte near the cathode. The other arrangements shown in FIGS. 14(B), 14(C), and 14(D) are for the same purpose.

Figure 14B:
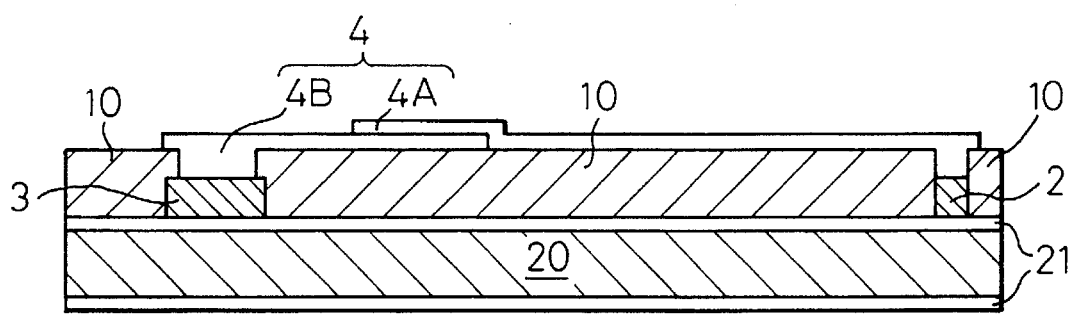
Figure 14C:
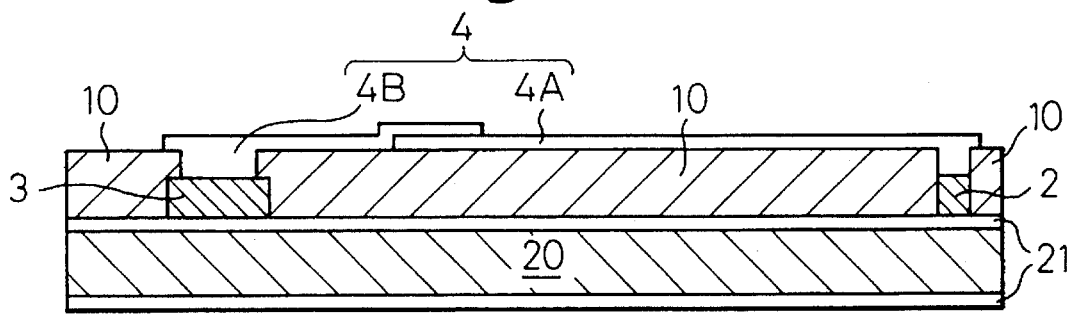
Figure 14D:
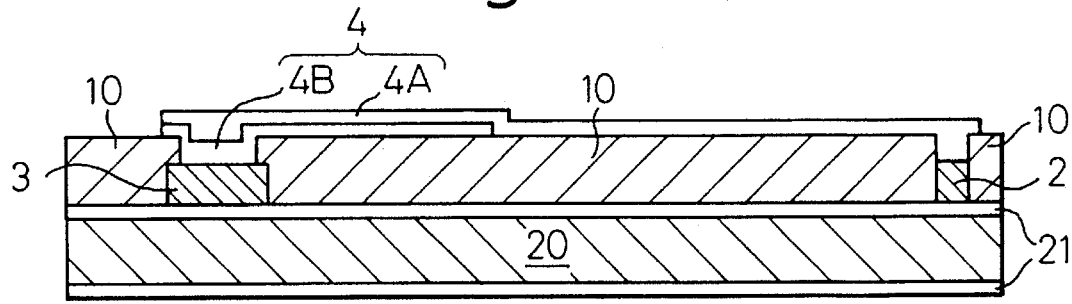
Figure 15A:
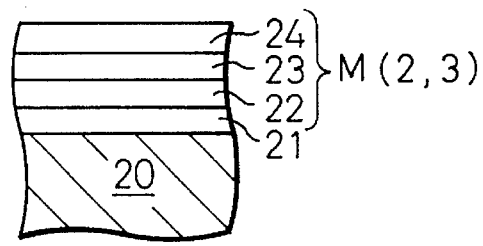
FIGS. 15(A), 15(B), 15(C), 15(D), and 15(E) are cross sectional views showing process steps for producing a miniaturized oxygen electrode having a double-layered electrolyte-containing material according to the present invention.
Figure 15B:
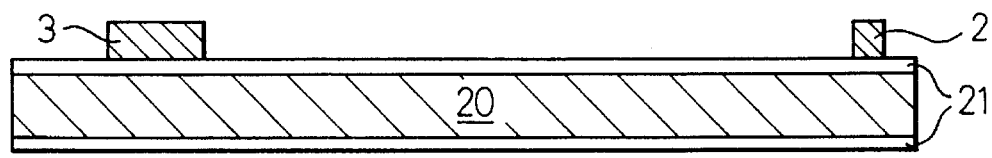
Figure 15C:
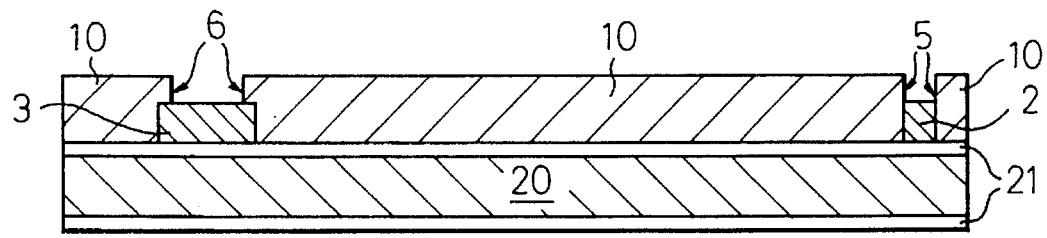
Figure 15D:
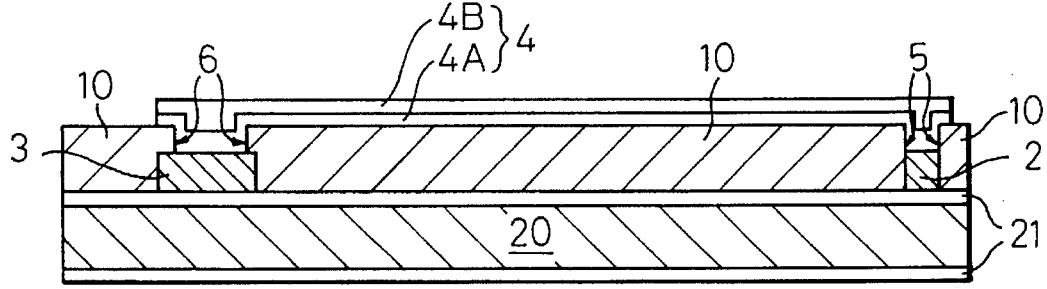
Figure 15E:
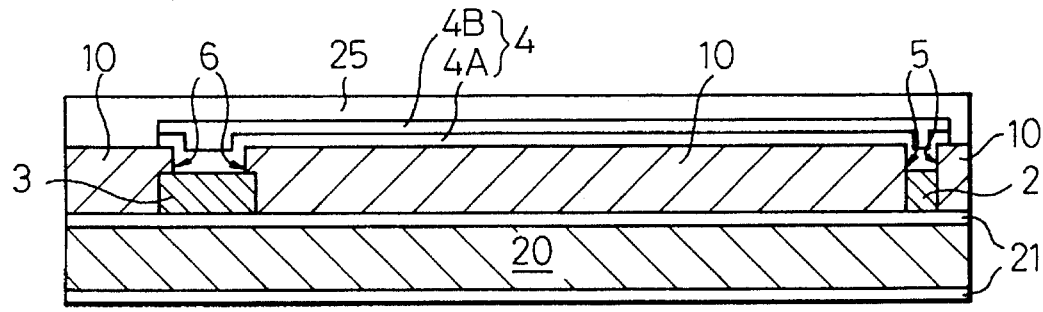

In the arrangements shown in FIGS. 14(B) and 14(C), a first layer 4A has one end connected to a cathode 2 and the other end terminating at an intermediate point between the cathode 2 and an anode 3, whereas a second layer 4B has one end connected to the anode 3 and the other end terminating at an intermediate point between the cathode 2 and the anode 3, and the first and second layers 4A and 4B overlap each other in the portions including the other ends thereof. In FIGS. 14(B) and 14(C), the first and second layers overlap in inverse orders. Namely, the arrangement (B) is obtained by first forming the second layer 4B and then forming the first layer 4B whereas the arrangement (C) is obtained by first forming the first layer 4A and then forming the second layer 4B. (See claim 4).

In the arrangement shown in FIG. 14(D), a second are 4B is provided in the region similar to those of the arrangements (B) or (C), whereas a first layer 4A, which is later formed, does not terminate at an intermediate point between a cathode 2 and an anode 3 but extends to the region in which the second layer 4B is connected to the anode 3.

Generally, an arrangement can be selected from the arrangements shown in FIGS. 14(A) to 14(D) so that the higher the electrolyte concentration, the closer to the anode 3 (i.e., more distant from the cathode 2) is the position of connection between the first and second layers 4A and 4B.

When the electrolyte concentration is further higher and almost equal to a saturation concentration, at least one of the first and second layers of the electrolyte-containing material preferably contains a component which forms a gel when water is introduced therein. When the resultant electrolyte solution is in a gel form, the diffusion of the electrolyte in the solution is retarded to promote prevention of the cathode deterioration during water introduction effected by high pressure water vapor sterilization or the like.

Advantageously, the gel is sufficiently hard so that the electrolyte is prevented from diffusing to the cathode during the water introduction, and is sufficiently soft so that, during the subsequent holding, the electrolyte diffuses to form a single electrolyte solution layer in a practically acceptable time and so that, during an oxygen measurement, an intermediate product generated in the reduction reaction of oxygen is rapidly dissipated so as not to substantially affect the oxygen measurement. Agarose is one of the most suitable components for gelation.

It is also advantageous that at least one of the first layer and the second layer of the electrolyte-containing material contains sodium alginate, at least one of the first layer and the second layer contains an alkaline earth metal salt, and the sodium alginate and the alkaline earth metal salt react during the water introduction to generate an alkaline earth metal alginate which acts as the component for gelation.

To provide a stable anode, it is preferable that the anode is composed of a silver/silver halide composite, that the electrolyte-containing material 4 contains a halogen ion as an electrolyte, and that at least one of the first layer and the second layer contains a trace amount of the same silver halide as in the anode.

This is preferable because, when the electrolyte consists of potassium chloride, the anode generally used is in the form of a composite electrode composed of 10 silver and an undissolvable halide such as silver/silver chloride or silver/silver bromide. To provide such a composite electrode through a reaction of a silver anode with an electrolyte, it is necessary that the electrolyte contains halogen ions. However, when the halogen ion concentration is high, a halide such as silver chloride, even if formed on the anode by the above-mentioned reaction, would form a complex, which undesirably dissolves in the electrolyte solution. To avoid this phenomenon, silver halide must be added to the electrolyte-containing material in advance.

From this point of view, it is suitable that the trace amount of silver halide contained in the electrolyte-containing material is present in a sufficient amount to suppress dissolution of a silver halide generated by an electrode reaction occurring on the anode.

Typically, the halogen ion is chloride ion and the silver halide is silver chloride, because these are easily commercially available and inexpensive.

In a preferred embodiment of the present invention, at least one of the first layer and the second layer of the electrolyte-containing material contains a trace amount of manganese dioxide to decompose hydrogen peroxide generated as an intermediate product in the reduction reaction of oxygen on the cathode. This ensures that measurement can be carried out at an improved stability.

When the electrolyte contains trace amounts of silver halide and/or manganese dioxide and also contains a component for gelation, the resultant gel is preferably sufficiently hard to fix and prevent settling of the silver halide and the manganese dioxide.

Also preferably, a second layer of the electrolyte-containing material is overlaid on a first layer only in the region of connection to an anode and contains an oxidizing agent such as ferric chloride in order to produce a silver halide on the anode.

Also preferably, at least one of the first layer and the second layer of the electrolyte-containing material contains a buffering agent to fix the pH value of the electrolyte.

It is possible that at least one of the first layer and the second layer is composed of plural layers having different chemical compositions. An electrolyte-containing material is prepared by blending various ingredients. The blending process must be performed for every desired compositions of the electrolyte-containing materials. The blending process takes several hours or more. According to the above embodiment, various compositions are prepared by blending ingredients in advance and some of the thus-prepared compositions are selectively combined in accordance with a desired composition of the electrolyte-containing material, so that is becomes unnecessary to blend various ingredients upon every preparation of the electrolyte-containing materials.

Example 8

Referring to FIGS. 15(A) to 15(E), a process of producing a miniaturized oxygen electrode according to the present invention will be described below. The miniaturized oxygen electrode has the same plan arrangement as that shown in FIG. 12(A) and has an electrolyte-containing material having a double-layered structure as shown in FIG. 13(A). Although only one miniaturized oxygen electrode is described for simplicity, a large number of miniaturized oxygen electrodes are actually formed on a single silicon wafer simultaneously.

Step 1: Forming Electrode Pattern (FIGS. 15(A) and 15(B))

A 400 μm thick, (100) plane silicon wafer 20 was cleaned with a mixed solution of hydrogen peroxide and ammonia and concentrated nitric acid.

The silicon wafer 20 was wet-oxidized at 1000° C. for 200 min to form a 0.8 μm thick $SiO_2$ insulating film 21 on both sides.

The following substeps (a) to (e) were carried out to form an electrode pattern M composed of the three layers of a chromium film 22, a gold film 23 and a silver film 24. The electrode pattern M includes the actual electrode portions of cathode 2 and anode 3, lead portions, and external connection terminal pads.

(a) A vacuum deposition process was carried out to form a chromium film 22 (400 Å thick) and a gold film 23 (1500 Å thick) on one side of the silicon wafer 20 in that order.

(b) On the entire surface of the silicon wafer 20, a positive photoresist (Tokyo Ohka Kogyo, OFPR-5000) was spin-coated, prebaked at 80° C. for 30 min, exposed to UV-light and developed to form a photoresist pattern as an etching mask.

(c) The gold film 23 and the chromium film 22 were sequentially etched with the following etchants, respectively, and the photoresist pattern was removed with acetone to form a chromium gold laminate film pattern corresponding to the patterns of the cathode 2 and the anode 3.

Etchant for gold: 1 g $I_2$+4 g KI+4 ml water

Etchant for chromium: 0.5 g NaOH+1 g $K_3Fe(CN)_6$+4 ml water (d) The wafer or substrate 20 was then cleaned in a hot aqueous solution of hydrogen peroxide and ammonia and the entire surface thereof was coated with the same photoresist as that used above. Thereafter, the substrate was prebaked at 80° C. for 30 min, exposed to light, immersed in toluene at 30° C. for 10 min, postbaked at 80° C. for 10 min, and developed. This process exposed the above-formed chromium/gold laminate pattern.

(e) A vacuum deposition process was carried out to form a silver film 24 entirely on the substrate. The photoresist was removed by immersing in acetone. A lift-off process was performed to remove the silver film 24 in the region other than the chromium/gold laminate film pattern.

Step 2: Defining Oxygen Sensing Site (FIG. 15(C))

A negative photoresist 10 (Tokyo Ohka Kogyo, OMR-83) was applied to the substrate except for the actual electrodes of cathode 2 and anode 3 (inside the openings 5 and 6 shown in FIG. 12(A)) and for the external connection terminal pad region 12 (FIG. 12(A)). This was carried out by applying a photoresist on the substrate, prebaking at 80° C. for 30 min, exposing to UV-light and developing, followed by a postbaking at 150° C. for 30 min.

Step 3: Forming Electrolyte-containing Material (FIG. 15(D))

The first layer 4A of an electrolyte-containing material 4 was formed by screen-printing a first composition consisting of a 50 wt % hexanol solution of polyvinylpyrrolidone (PVP) and not containing electrolytes on the substrate in the regions of the cathode 2, the anode 3 and the conducting portion electrically connecting the cathode 2 and the anode 3, and then baking at 80° C. for 10 min. Then, over the entire length of the first layer 4A, a second composition, consisting of a hexanol solution of 50 wt % polyvinylpyrrolidone in which an electrolyte of 3 wt % potassium chloride powder and a buffering agent of 3 wt % tris(hydroxymethyl)aminomethane are dispersed, was screen-printed and baked at 80° C. for 2 hours to form the second layer 4B of the electrolyte-containing material 4.

Step 4: Forming Gas-permeable Membrane (FIG. 15(E))

The following substeps (a) to (d) were carried out to form a gas-permeable membrane 25.

Figure 12B:
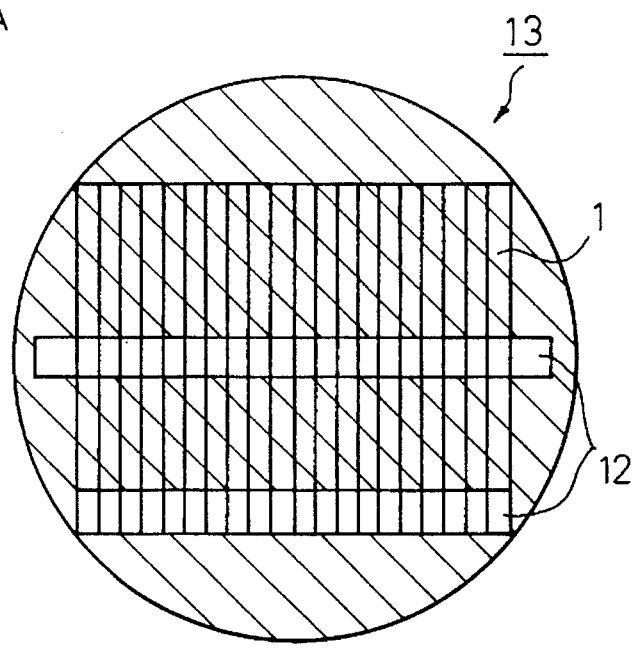

(a) A thermosetting release coating (Fujikura Kasei Col. XB-801) was screen-printed at the pad region (FIG. 12(A), 12) to a thickness of 100 μm and cured by heating at 80° C. for 20 min to form a mask or a removable cover film.

(b) A silicone resin (Toray-Dow Corning Co. SE9176) as a component of the gas-permeable membrane was spin-coated on the substrate and was cured by heating at 80° C. for 60 min in a oven humidified by water contained in a petri dish or a beaker placed in the oven.

(c) The mask formed on the pad region was peeled off with a pincette to remove the silicone resin in that region, and thereby expose the pad region 12 (pads 7 and 8). This completed a miniaturized oxygen electrode of the present invention covered with the gas-permeable membrane 25 except for the pad region 12.

A number of miniaturized oxygen electrodes thus collectively formed on the silicon wafer 20 were cut into chips by a dicing saw.

Example 9

A miniaturized oxygen electrode of the present invention was produced in the same manner as used in Example 8, except that, in step 3 (forming electrolyte-containing material), 1 wt % agarose was added to the first and second compositions to form a gel upon water introduction.

Example 10

Step 1: Forming Electrode Patterns

Electrode patterns 2 and 3 were formed in the same way as used in Example 8, step 1.

Step 2: Defining Oxygen Sensing Site by Photoresist

A negative photoresist layer 10 was formed in the same way as used in Example 8, step 2.

Step 3: Forming Electrolyte-containing Material

The first layer 4A of an electrolyte-containing material 4 was formed by screen-printing a first composition consisting of a hexanol solution of 50 wt % polyvinylpyrrolidone (PVP) and 1 wt % silver chloride on the substrate in the regions of the cathode 2, the anode 3 and the conducting portion electrically connecting the cathode and the anode, and then baking at 80° C. for 10 min. Then, on the first layer 4A only in the region above and near the anode 3, a second composition, consisting of a hexanol solution of 50 wt % polyvinylpyrrolidone in which an electrolyte of a 3 wt % potassium chloride powder, a buffering agent of 3 wt % tris(hydroxymethyl)aminomethane, a buffering agent of 1 wt % glycine, 1 wt % silver chloride, and 1 wt % manganese dioxide are dispersed, was screen-printed and baked at 80° C. for 2 hours to form the second layer 4B of the electrolyte-containing material 4. This provided the electrolyte-containing material 4 composed of the first layer 4A of the first composition and the second layer 4B of the second composition.

Step 4: Forming Gas-permeable Membrane

A gas-permeable membrane was formed in the same manner as used in Example 8, in step 4.

Example 11

A miniaturized oxygen electrode of the present invention was produced in the same manner as used in Example 10, except that, in step 3 (forming electrolyte-containing material), 0.1 wt % ferric chloride was added to the second composition to promote generation of silver chloride near the anode 3.

Example 12

A miniaturized oxygen electrode of the present invention was produced in the same manner as used in Example 10, except that, in step 3 (forming electrolyte-containing material), 0.4 wt % alginic acid and 2 wt % calcium chloride were added to both the first and second compositions to induce a reaction therebetween to form calcium alginate, thereby forming a gel.

Comparative Example

A miniaturized oxygen electrode was produced in the same manner as used in Example 10, except that, in step 3 (forming electrolyte-containing material), a single composition including all ingredients of the first and second compositions used in Example 10 was screen-printed and baked at 80° C. for 2 hours to form a single-layered electrolyte-containing material 4 as shown in FIG. 13(B).

Figure 16:
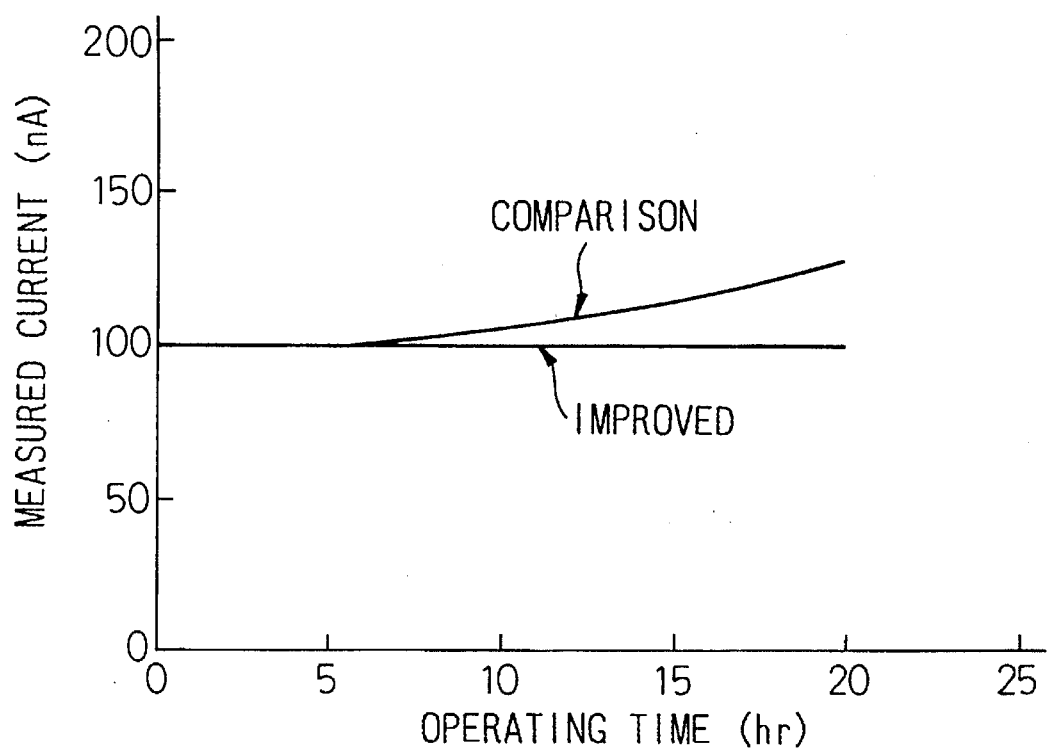
FIG. 16 is a graph showing the measured current values during a long-term continuous operation of miniaturized oxygen electrodes having double- and single-layered electrolyte-containing materials.

The miniaturized oxygen electrodes produced by Example 10 and Comparative Example were compared in terms of the stability of the measured current. FIG. 16 shows the currents measured by these miniaturized oxygen electrodes when continuously operated in air-saturated water. The improved miniaturized oxygen electrode having a double-layered electrolyte-containing material (Example 10) provided a constant current throughout a continuous operation for 20 hours whereas the comparative miniaturized oxygen electrode having a single-layered electrolyte-containing material (Comparative Example) exhibited a gradual increase in the measured current after being operated for 5 hours.

As herein above described, the present invention provides a further improved miniaturized oxygen electrode having an improved stability for an extended continuous operation.

We claim:

1. A miniaturized oxygen electrode comprising:
   an electrically insulating substrate;
   an electrolyte-containing material disposed on said substrate to form an electrolyte solution when water is introduced thereto;
   a set of component electrodes disposed on said substrate and connected with each other via said electrolyte-containing material;
   a gas-permeable membrane covering said electrolyte-containing material;
   said set of component electrodes including a cathode on which a reduction reaction of oxygen occurs and an anode as a counterpart of said cathode;
   said electrolyte-containing material is composed of a first layer and a second layer which are mutually connected, said first layer containing no electrolytes and being connected to said cathode and said second layer containing an electrolyte and being not connected to said cathode, said mutual connection of said first layer and said second layer being effected so that, during said water introduction and a subsequent holding, said electrolyte of said second layer diffuses to said first layer to form a single electrolyte solution layer.

2. A miniaturized oxygen electrode according to claim 1, wherein said electrolyte-containing material is composed of said first layer connected at both ends to said cathode and said anode, respectively, and of said second layer laminated on said first layer over the entire length of the first layer.

3. A miniaturized oxygen electrode according to claim 1, wherein said electrolyte-containing material is composed of said first layer connected at both ends to said cathode and said anode, respectively, and of said second layer laminated on said first layer only in and near a region of connection of said first layer with said anode.

4. A miniaturized oxygen electrode according to claim 3, wherein said second layer, which is laminated on said first layer only in and near a region of connection of said first layer to said anode, contains an oxidizing agent to generate a silver halide on said anode.

5. A miniaturized oxygen electrode according to claim 4, wherein said oxidizing agent is composed of ferric chloride.

6. A miniaturized oxygen electrode according to claim 1, wherein said electrolyte-containing material is composed of said first layer connected at one end to said cathode and said second layer connected at one end to said anode, said first layer and said second layer being connected to each other in a region including the other ends thereof.

7. A miniaturized oxygen electrode according to any one of claims 1 to 3 or 6, wherein said anode is composed of a silver/silver halide composite, said electrolyte-containing material contains a halogen ion as an electrolyte, and at least one of said first layer and said second layer contains a trace amount of the same silver halide as that of said anode.

8. A miniaturized oxygen electrode according to claim 7, wherein said trace amount of silver halide contained in said electrolyte-containing material is present in an amount to suppress dissolution of a silver halide generated by an electrode reaction occurring on said anode.

9. A miniaturized oxygen electrode according to claim 5, wherein said halogen ion is chloride ion and said silver halide is silver chloride.

10. A miniaturized oxygen electrode according to claim 7, wherein at least one of said first layer and said second layer of said electrolyte-containing material contains a component which brings said electrolyte solution layer formed by said water introduction into a gel having a hardness high enough to fix and suppress settling of said silver halide.

11. A miniaturized oxygen electrode according to any one of claims 1 to 3 or 6, wherein at least one of said first layer and said second layer of said electrolyte-containing material contains a trace amount of manganese dioxide to decompose hydrogen peroxide generated as an intermediate product in the reduction reaction of oxygen on said cathode.

12. A miniaturized oxygen electrode according to claim 11, wherein at least one of said first layer and said second layer of said electrolyte-containing material contains a component which brings said electrolyte solution layer formed by said water introduction into a gel having a hardness high enough to fix and suppress settling of said manganese dioxide.

13. A miniaturized oxygen electrode according to any one of claims 1 to 3 or 6, wherein at least one of said first layer and said second layer of said electrolyte-containing material contains a component which brings said electrolyte solution layer formed by said water introduction into a gel.

14. A miniaturized oxygen electrode according to claim 13, wherein said gel is hard enough so that said electrolyte is prevented from diffusing to said cathode during said water introduction, and is soft enough so that, during said subsequent holding, said electrolyte diffuses to form single electrolyte solution layer in a practically acceptable time and so that, during an oxygen measurement, an intermediate product generated in said reduction reaction of oxygen is rapidly dissipated so that the oxygen measurement is not substantially affected.

15. A miniaturized oxygen electrode according to claim 13, wherein said component for gelation is agarose.

16. A miniaturized oxygen electrode according to claim 13, wherein at least one of said first layer and said second layer of said electrolyte-containing material contains sodium alginate, at least one of said first layer and said second layer contains an alkaline earth metal salt, and said sodium alginate and said alkaline earth metal salt react during said water introduction to generate an alkaline earth metal alginate which act as said component for gelation.

17. A miniaturized oxygen electrode according to any one of claims 1 to 3 or 6, wherein at least one of said first layer and said second layer of said electrolyte-containing material contains a buffering agent to fix the pH value of said electrolyte.

18. A miniaturized oxygen electrode according to any one of claims 1 to 3 or 6, wherein at least one of said first layer and said second layer is composed of plural layers having different chemical compositions.

* * * * *

UNITED STATES PATENT AND TRADEMARK OFFICE
CERTIFICATE OF CORRECTION

PATENT NO. : 5,492,611
DATED : February 20, 1996
INVENTOR(S) : Akio SUGAMA et al.

It is certified that error appears in the above-indentified patent and that said Letters Patent is hereby corrected as shown below:

```
Column 12, line 30, delete "en" and substitute --an--;
           line 63, after "thin" insert --layer--.
Column 13, line 6, delete "FIGS." and substitute --(FIGS.--
           line 39, delete "(j2)" and substitute --(j2))--
           line 55, delete "(k3)" and substitute --(k3))--
Column 14, line 20, delete "(n2)" and substitute --(n2))--
Column 17, line 26, delete "FIG." and substitute --(FIG.--
```

Signed and Sealed this

Eleventh Day of June, 1996

*Attest:*

BRUCE LEHMAN

*Attesting Officer*    Commissioner of Patents and Trademarks